United States Patent
Sakuma et al.

(10) Patent No.: US 6,787,552 B2
(45) Date of Patent: Sep. 7, 2004

(54) PPAR DELTA ACTIVATORS

(75) Inventors: Shogo Sakuma, Saitama (JP); Tsuyoshi Endo, Tokyo (JP); Atsushi Tendo, Saitama (JP); Toshihiro Takahashi, Saitama (JP); Shinichi Yoshida, Chiba (JP); Kunio Kobayashi, Saitama (JP); Nobutaka Mochizuki, Chiba (JP); Tomio Yamakawa, Chiba (JP); Takashi Kanda, Saitama (JP); Seiichiro Masui, Saitama (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 10/344,496

(22) PCT Filed: Aug. 9, 2001

(86) PCT No.: PCT/JP01/06836

§ 371 (c)(1),
(2), (4) Date: Feb. 11, 2003

(87) PCT Pub. No.: WO02/14291

PCT Pub. Date: Feb. 21, 2002

(65) Prior Publication Data

US 2004/0097739 A1 May 20, 2004

(30) Foreign Application Priority Data

Aug. 11, 2000 (JP) ........................ 2000-243596
Dec. 28, 2000 (JP) ........................ 2000-402893

(51) Int. Cl.[7] ................. A61K 31/421; A61K 31/426; C07D 233/06; C07D 263/32; C07D 277/24
(52) U.S. Cl. ................. 514/256; 514/311; 514/340; 514/342; 514/365; 514/374; 514/376; 514/398; 514/400; 544/333; 546/167; 546/270.4; 546/271.4; 548/187; 548/204; 548/225; 548/236; 548/323.5; 548/333.5; 548/338.1; 548/341.5; 548/343.5
(58) Field of Search ................. 514/398, 400, 514/256, 311, 340, 342, 365, 374, 376; 548/323.5, 333.5, 338.1, 341.5, 343.5, 187, 204, 225, 236; 546/270.4, 271.4, 167; 544/333

(56) References Cited

U.S. PATENT DOCUMENTS

| | | | | | |
|---|---|---|---|---|---|
| 3,912,756 | A | * | 10/1975 | Wolff et al. | 548/492 |
| 5,262,540 | A | * | 11/1993 | Meanwell | 514/374 |
| 6,417,212 | B1 | * | 7/2002 | Brooks et al. | 514/374 |
| 6,506,757 | B1 | * | 1/2003 | Tajima et al. | 514/254.02 |
| 6,518,290 | B1 | * | 2/2003 | Sierra | 514/365 |

FOREIGN PATENT DOCUMENTS

| EP | 558062 | * | 9/1993 |
|---|---|---|---|
| WO | WO-92/10468 | * | 6/1992 |
| WO | WO-97/28115 | * | 8/1997 |

OTHER PUBLICATIONS

Meanwell et al., Journal of Medicinal Chemistry, 35(19), 3483–3497, 1992.*

* cited by examiner

Primary Examiner—Fiona T. Powers
(74) Attorney, Agent, or Firm—Reed Smith LLP

(57) ABSTRACT

Compounds of the general formula (I) or salts thereof and activators of PPARδ (peroxisome proliferator activated receptor δ) containing the compounds or the salts as the active ingredient: wherein $R^1$ and $R^2$ each are hydrogen, $C_{1-8}$ alkyl, an aryl or heterocyclic group which may be substituted, or the like; A is oxygen, sulfur, or the like; $X^1$ and $X^2$ are each a free valency, oxygen, $S(O)_p$ (wherein p is an integer of 0 to 2), $C(=O)$, $C(=O)NH$, $NHC(=O)$, $CH=CH$, or the like; Y is optionally substituted $C_{1-8}$ alkylene; Z is oxygen or sulfur; $R^3$ and $R^4$ are each optionally substituted $C_{1-8}$ alkyl; and $R^8$ is hydrogen or $C_{1-8}$ alkyl, with the proviso that when $X^1$ is a free valency, $X^2$ is not O or $S(O)_p$, while when $X^1$ is $C(=O)NH$, $X^2$ is not a free valency.

(I)

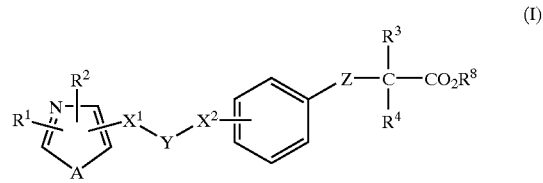

34 Claims, No Drawings

PPAR DELTA ACTIVATORS

CROSS-REFERENCES TO RELATED APPLICATIONS

This application claims priority of Japanese International Application No. PCT/JP01/06836 filed Aug. 9, 2001 which claims the priority of Japanese International Application Nos. 2000-243596 filed Aug. 11, 2000 and 2000-402893 filed Dec. 28, 2000, the complete disclosures of which are hereby incorporated by reference.

FIELD OF THE INVENTION

The present invention relates to an activator of peroxisome proliferator activated receptor δ.

BACKGROUND OF THE INVENTION

The peroxisome is a small organ present in cells of animals and plants, and its matrix contains various enzymes such as catalase. The peroxisome proliferator is a substance inducing proliferation of the peroxisome. Various compounds such as fibrates, herbicides, and phthalic acid plasticizers are known to be able to induce proliferation of peroxisome.

Isseman, et al. have identified a nuclear receptor which is activated by the peroxisome proliferator and given a name of peroxisome proliferator activated receptor (PPAR).—Nature, 347, p645–650, 1990.

As PPAR, three subtypes such as PPARα, PPARγ and PPARδ have been identified until now.—Proc. Natl. Acad. Sci. USA, 91, p7335–7359, 1994.

The above-mentioned fibrates are a class of TG (triglyceride) lowering drugs that mediate their clinical effects through activation. Further, thiazolidine compounds (Troglitazone, Rosiglitazone, Pioglitazone) useful in the treatment of diabetes are also known as ligands of PPARγ.

As a pharmaceutical having PPARδ activating effect, there are known GW-2433 (Glaxo Wellcome), L-165041 (Merck), and YM-16638 (Yamanouchi Pharmaceutical each having the following formula:

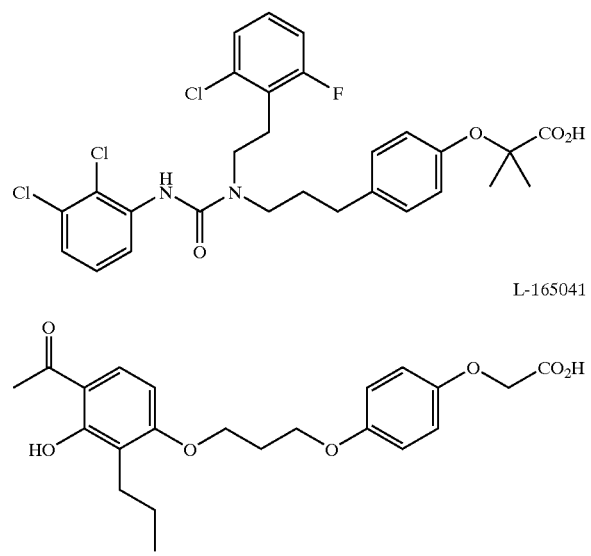

GW-2433

L-165041

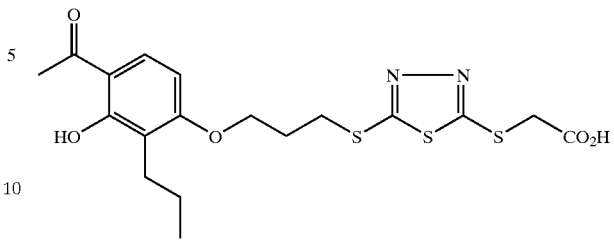

YM-16638

WO 92/10468 describes that GW-2433 can be employable for prevention and treatment of atherosclerosis.

WO 97/28115 describes that L-165041 can be employable for treatment of diabetes and suppression of obesity.

WO 99/04815 describes that YM-1663B shows effects for reducing serum cholesterol and reducing LDL cholesterol.

Recently, JBC, 272(6), p3406–3410, 1997 and Cell, 99, p335–345, 1999 describe proposal for application of PPAR δ ligand as an anti-cancer agent and an anti-inflammatory agent.

European Patent 558 062 describes the following compound A which has a structure similar to that of the general formula (II) [mentioned below] representing an oxazole derivative of the invention:

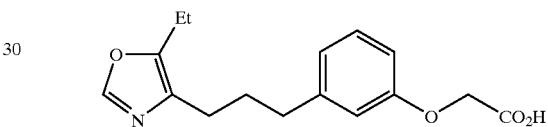

J. Immunol. Methods, 207(1), 23–31, 1997 describes a compound B having the following formula:

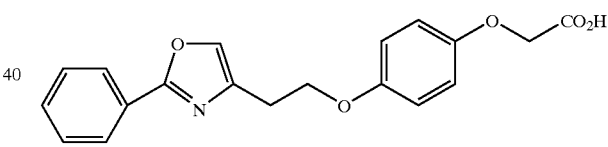

All of the oxazole derivatives identified by the compound A, compound B and the general formula (II) of the invention may be described as compounds of phenoxyacetic acid type. However, there are clear structural difference between the compounds A, B and the compound of the invention, that is, the compounds A, B have no substituents at the α-site, while the compound of the invention is a compound of α,α-dialkylphenoxy type.

In addition, while the above-mentioned EP 558 062 teaches that the compound A is of value for treatment of hyperthrombinemia and as blood pressure depressant, no mention is given with respect to an effect as PPARδ ligand. Further, while the J. Immunol. Methods teaches the use of the compound B as blood pressure depressant, there is no concrete description to teach that the compound is effective as PPARδ ligand.

Recently, WO 01/40207 describes a substituted oxa(thia)zole derivative showing an agonist action for PPAR α, and WO 01/16120 describes an oxa(thia)zole derivative substituted with a biaryl group which is employable as a PPAR controlling agent.

In comparison with the compounds of the invention, the compound of WO 01/40207 has C(=O)NH as $X^1$ and a bond as $X_2$, and the compound of WO 01/16120 has a bond as $X^1$ and O, X or the like as $X^2$. Accordingly, the structural difference is clear.

The present invention provides a compound having the below-mentioned general formula (I), an oxazole derivative having the below-mentioned general formula (II), and a thiazole derivative having the below-mentioned general formula (III), all of which has an action as activator of peroxisome proliferator activated receptor δ.

DISCLOSURE OF THE INVENTION

The invention resides in a compound having the following general formula (I) or a salt thereof:

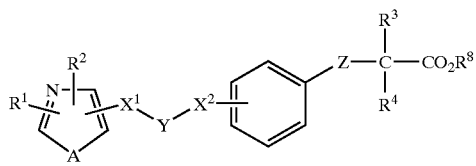
(I)

[wherein each of $R^1$ and $R^2$ independently is a hydrogen atom, an alkyl group having 1–8 carbon atoms, an alkyl group having 1–8 carbon atoms and a halogen atom substituent, an alkenyl group having 2–8 carbon atoms, an alkynyl group having 2–8 carbon atoms, a 3–7 membered cycloalkyl group, an alkyl group having 1–8 carbon atom and a 3–7 membered substituent, an arylalkyl group that has a $C_{6-10}$ aryl portion and $C_{1-4}$ alkyl portion and optionally has a substituent, or an aryl or heterocyclic group which optionally has a substituent; A is O, S, or $NR^5$ in which $R^5$ is H or $C_{1-8}$ alkyl; each of $X^1$ and $X^2$ independently is a bond (free valency), O, S $(O)_p$ in which p is an integer of 0 to 2, C(=O), C(=N—$OR^6$) in which $R^6$ is H or $C_{1-8}$ alkyl; C(=O)NH, NHC(=O), $SO_2NH$, $NHSO_2$, CH($OR^7$) in which $R^7$ is H or $C_{1-8}$ alkyl, CH=CH, or C≡C; Y is an alkylene chain having 1–8 carbon atoms and optionally a substituent; Z is O or S; each of $R^3$ and $R^4$ independently is an alkyl group having 1–8 carbon atoms and optionally a substituent; and $R^8$ is a hydrogen atom or an alkyl group having 1–8 carbon atoms; provided that $X^2$ is neither O nor $S(O)_p$ when $X^1$ is a bond, while $X^2$ is not a bond when $X^1$ is C(=O)NH].

Further, the invention provides an oxazole derivative having the following formula (II) or a salt thereof:

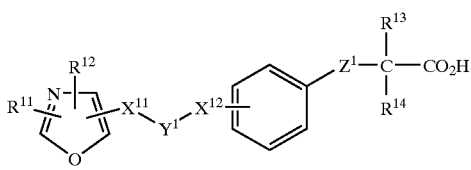
(II)

[wherein each of $R^{11}$ and $R^{12}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{11}$ and $X^{12}$ independently is a bond, $S(O)_q$ in which q is an integer of 0 to 2, C(=O), C(=N—$OR^{16}$) in which $R^{16}$ is H or $C_{1-8}$ alkyl; C(=O)NH, NHC(=O), $SO_2NH$, $NHSO_2$, CH($OR^{17}$) in which $R^{17}$ is H or $C_{1-8}$ alkyl, CH=CH, or C≡C; $Y^1$ is an alkylene chain having 1–8 carbon atoms and optionally a $C_{1-8}$ alkyl or $C_{1-8}$ alkoxy substituent; $Z^1$ is O or S; each of $R^{13}$ and $R^{14}$ independently is an alkyl group having 1–8 carbon atoms and optionally a halogen or $C_{1-8}$ alkoxy substituent; provided that $X^{12}$ is neither O nor $S(O)_q$ when $X^{11}$ is a bond, while $X^{12}$ is not a bond when $X^{11}$ is C(=O)NH].

Furthermore, the invention provides a thiazole derivative having the following formula (III) or a salt thereof:

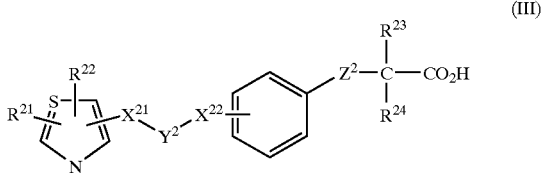
(III)

[wherein each of $R^{21}$ and $R^{22}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{21}$ and $X^{22}$ independently is a bond, $S(O)_r$ in which r is an integer of 0 to 2, C(=O), C(=N—$OR^{26}$) in which $R^{26}$ is H or $C_{1-8}$ alkyl; C(=O)NH, NHC(=O), $SO_2NH$, $NHSO_2$, CH($OR^{27}$) in which $R^{27}$ is H or $C_{1-8}$ alkyl, CH=CH, or C≡C; $Y^2$ is an alkylene chain having 1–8 carbon atoms and optionally a $C_{1-8}$ alkyl or $C_{1-8}$ alkoxy substituent; $Z^2$ is O or S; each of $R^{23}$ and $R^{24}$ independently is an alkyl group having 1–8 carbon atoms and optionally a halogen or $C_{1-8}$ alkoxy substituent; provided that $X^{22}$ is neither O nor $S(O)_r$ when $X^{21}$ is a bond, while $X^{22}$ is not a bond when $X^{21}$ is C(=O)NH].

Furthermore, the invention provides an activator of peroxisome proliferator activated receptor δ which contains as an effective component a compound of the formula (I), an oxazole derivative of the formula (II), or a thiazole derivative of the formula (III) or their salts.

PREFERRED EMBODIMENTS OF THE INVENTION

The present invention is described below in more detail.

The meanings of the symbols in the formula (I) are described below.

In the formula (I), examples of the alkyl groups having 1–8 carbon atoms for $R^1$, $R^2$, $R^5$, $R^6$, $R^7$ and $R^8$ include methyl, ethyl, propyl, isopropyl, butyl, isobutyl, t-butyl and pentyl.

Examples of the alkyl groups having 1–8 carbon atoms and a halogen substituent for $R^1$ and $R^2$ include methyl, ethyl, propyl, isopropyl, butyl, and t-butyl which are substituted with 1–3 halogens such as fluorine, chlorine, and bromine. Preferred are trifluoromethyl, chloromethyl, 2-chloroethyl, 2-bromoethyl and 2-fluoroethyl.

Examples of the alkenyl groups having 2–8 carbon atoms for $R^1$ and $R^2$ include vinyl and allyl.

Examples of the alkynyl groups having 2–8 carbon atoms for $R^1$ and $R^2$ include propargyl.

Examples of the 3–7 membered cycloalkyl group for $R^1$ and $R^2$ include cyclohexyl and cyclopentyl.

Examples of the alkyl groups having 1–8 carbon atoms and a 3–7 membered cycloalkyl substituent for $R^1$ and $R^2$ include cyclohexylmethyl and cyclopentylmethyl.

Examples of the arylalkyl groups (having $C_{6-10}$ aryl portion and $C_{1-4}$ alkyl portion) which optionally contain a substituent for $R^1$ and $R^2$ include alkyl groups having 1–4 carbon atoms substituted with a phenyl or naphthyl group which can have a substituent selected from the group consisting of halogens (e.g., fluorine, chlorine, bromine), hydroxyl, nitro, amino, $C_{1-8}$ alkyl groups (e.g., methyl, ethyl, propyl, isopropyl, butyl, isobutyl, t-butyl), $C_{1-8}$ alkyl groups substituted with 1–3 halogen atoms (e.g., trifluoromethyl, trifluoroethyl), $C_{1-8}$ alkoxy groups (e.g., methoxy, ethoxy), $C_{1-8}$ alkyl groups substituted with 1–3 halogen atoms (e.g., 2-chloroethoxy), phenyl, benzyl, phenyloxy, benzoyl, and pyridyl. Preferred are methyl or ethyl group substituted with phenyl which can have a substituent of $C_{1-6}$ alkyl (e.g., methyl, ethyl, propyl), $C_{1-6}$ alkoxy (methoxy, ethoxy), or halogen (fluorine, chlorine, bromine). More preferred are benzyl, benzhydryl, and phenethyl.

Examples of the aryl groups optionally having a substituent for $R^1$ and $R^2$ include a phenyl or naphthyl group which can have a substituent selected from the group consisting of halogens (fluorine, chlorine, bromine), hydroxyl, nitro, amino, substituted amino (dimethylamino), $C_{1-8}$ alkyl groups (methyl, ethyl, propyl, isopropyl, butyl, isobutyl, t-butyl), $C_{1-8}$ alkyl groups substituted with 1–3 halogen atoms (trifluoromethyl, trifluoroethyl), $C_{1-8}$ alkoxy groups (methoxy, ethoxy), $C_{1-8}$ alkyl groups substituted with 1–3 halogen atoms (e.g., 2-chloroethoxy), acyl (acetyl, benzoyl), carboxyl, phenyl, benzyl, phenyloxy or pyridyl. Preferred are phenyl, 2-chlorophenyl, 3-chlorophenyl, 4-chlorophenyl, 2,3-dichlorophenyl, 2,4-dichlorophenyl, 2,6-dichlorophenyl, 2-fluorophenyl, 2-trifluoromethylphenyl, 4-chloro-2-hydroxyphenyl, 2-methylphenyl, 4-butylphenyl and naphthyl.

Examples of the heterocyclic groups optionally having a substituent for $R^1$ and $R^2$ include 5–8 membered heterocyclic groups having 1–3 ring-forming hetero atoms selected from the group of nitrogen atom, oxygen atom and sulfur atom and remaining carbon atoms, such as pyridyl, thienyl furyl, and thiazolyl, and further include condensed ring groups formed of these heterocyclic ring and benzene ring, such as quinolyl, benzofuranyl and benzothienyl. These heterocyclic groups can have a substituent such as that described for the aryl group having a substituent for $R^1$ and $R^2$.

Y is an alkylene chain which has 1–8 carbon atoms and may be substituted with $C_{1-8}$ alkyl (e.g., methyl, ethyl, propyl) or $C_{1-8}$ alkoxy (methoxy, ethoxy). Preferred are alkylene chains having 1–6 carbon atoms. More preferred are methylene, ethylene, and propylene.

Examples of the alkyl groups having 1–8 carbon atoms and optionally containing a substituent for $R^3$ and $R^4$ include alkyl groups having 1–8 carbon atoms which may have a halogen atom (e.g., fluorine, chlorine, bromine) or $C_{1-8}$ alkoxy (e.g., methoxy, ethoxy). Preferred are methyl, ethyl, and propyl.

The meanings of the symbols in the formula (II) are described below.

In the formula (II), examples of the alkyl groups having 1–8 carbon atoms for $R^{11}$, $R^{12}$, $R^{15}$, $R^{16}$ and $R^{17}$ include methyl, ethyl, propyl, isopropyl, butyl, isobutyl, t-butyl and pentyl.

Examples of the alkyl groups having 1–8 carbon atoms and a halogen substituent for $R^1$ and $R^2$ include methyl, ethyl, propyl, isopropyl, butyl, and t-butyl which are substituted with 1–3 halogens such as fluorine, chlorine, and bromine. Preferred are trifluoromethyl, chloromethyl, 2-chloroethyl, 2-bromoethyl and 2-fluoroethyl.

Examples of the alkenyl groups having 2–8 carbon atoms for $R^{11}$ and $R^{12}$ include vinyl and allyl.

Examples of the alkynyl groups having 2–8 carbon atoms for $R^{11}$ and $R^{12}$ include propargyl.

Examples of the 3–7 membered cycloalkyl group for $R^{11}$ and $R^{12}$ include cyclohexyl and cyclopentyl.

Examples of the alkyl groups having 1–8 carbon atoms and a 3–7 membered cycloalkyl substituent for $R^{11}$ and $R^{12}$ include cyclohexylmethyl and cyclopentylmethyl.

Examples of the phenylalkyl (having $C_{1-4}$ alkyl portion), phenyl, naphthyl, pyridyl, thienyl, furyl, quinolyl, benzofuranyl and benzothienyl groups for $R^{11}$ and $R^{12}$ may contain a substituent of halogen (e.g., fluorine, chlorine, bromine), hydroxyl, nitro, amino, $C_{1-8}$ alkyl (e.g., methyl, ethyl, propyl), $C_{1-8}$ alkyl substituted with 1–3 halogen atoms (e.g., trifluoromethyl, trifluoroethyl), $C_{1-8}$ alkoxy (e.g., methoxy, ethoxy), $C_{1-8}$ alkoxy substituted with 1–3 halogen atoms (e.g., chloroethoxy), phenyl, benzyl, phenyloxy, benzoyl, or pyridyl. The phenylalkyl group (having 1–4 carbon atoms) can be benzyl, benzhydryl and phenethyl.

$Y^1$ is an alkylene chain which has 1–8 carbon atoms and may be substituted with $C_{1-8}$ alkyl (e.g., methyl, ethyl, propyl) or $C_{1-8}$ alkoxy (methoxy, ethoxy). Preferred are alkylene chains having 1–6 carbon atoms. More preferred are methylene, ethylene, and propylene.

Examples of the alkyl groups having 1–8 carbon atoms and optionally containing a substituent for $R^{13}$ and $R^{14}$ include alkyl groups having 1–8 carbon atoms which may have a halogen atom (e.g., fluorine, chlorine, bromine) or $C_{1-8}$ alkoxy (e.g., methoxy, ethoxy). Preferred are methyl, ethyl, and propyl.

The meanings of the symbols in the formula (III) are described below.

$R^{21}$, $R^{22}$, $R^{25}$, $R^{26}$, $R^{27}$ and $Y^2$ of the formula (III) are those described for $R^{11}$, $R^{12}$, $R^{15}$, $R^{16}$, $R^{17}$ and $Y^1$ of the formula (II).

(1) A preferred compound of the invention is an oxazole derivative of the formula (II) in which $X^{11}$ is a bond, and its salt.

(2) Another preferred compound of the invention is an oxazole derivative of the formula (II) or of (1) above in which $X^{12}$ is a bond, C(=O), C(=N—OH), C(=O)NH, NHC(=O), CH(OH) or CH=CH, and its salt.

(3) A further preferred compound of the invention is an oxazole derivative of the formula (II) or of (1) or (2) in which $R^{11}$ is a phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl, and its salt.

(4) A still further preferred compound of the invention is an oxazole derivative of the formula (II) or of (1) or (2) in which $R^{11}$ is phenyl, 2-chlorophenyl, 3-chlorophenyl, 4-chlorophenyl, 2,3-dichlorophenyl, 2,4-dichlorophenyl, 2,6-dichlorophenyl, 2-fluorophenyl, 2-trifluoromethylphenyl, 4-chloro-2-hydroxyphenyl, 2-methylphenyl, 4-butylphenyl or naphthyl, and its salt.

(5) A still further preferred compound of the invention is an oxazole derivative of the formula (II) or of (1)–(4) above in which $R^{12}$ is an alkyl group having 1–8 carbon atoms, or an alkyl group having 1–8 carbon atoms and 1–3 halogen atom substituents, and its salt.

(6) A still further preferred compound of the invention is an oxazole derivative of the formula (II) or of (1)–(5) above in which $R^{12}$ is attached to the 2-position of the oxazole ring, and its salt.

(7) A still further preferred compound of the invention is a thiazole derivative of the formula (III) in which $X^{21}$ is a bond, and its salt.

(8) A still further preferred compound of the invention is a thiazole derivative of the formula (III) or of (7) above in which $X^{22}$ is a bond, C(=O), C(=N—OH), C(=O)NH, NHC(=O), CH(OH) or CH=CH, and its salt.

(9) A still further preferred compound of the invention is a thiazole derivative of the formula (III) or of (7) or (8) in which $R^{21}$ is a phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl, and its salt.

(10) A still further preferred compound of the invention is a thiazole derivative of the formula (III) or of (7) or (8) in which $R^{21}$ is phenyl, 2-chlorophenyl, 3-chlorophenyl, 4-chlorophenyl, 2,3-dichlorophenyl, 2,4-dichlorophenyl, 2,6-dichlorophenyl, 2-fluorophenyl, 2-trifluoromethylphenyl, 4-chloro-2-hydroxyphenyl, 2-methylphenyl, 4-butylphenyl or naphthyl, and its salt.

(11) A still further preferred compound of the invention is a thiazole derivative of the formula (III) or of (7)–(10) above in which $R^{22}$ is an alkyl group having 1–8 carbon atoms, or an alkyl group having 1–8 carbon atoms and 1–3 halogen atom substituents, and its salt.

(12) A still further preferred compound of the invention is a thiazole derivative of the formula (III) or of (7)–(10) above in which $R^{22}$ is attached to the 2-position of the oxazole ring, and its salt.

The compounds of the invention having the formula (I) can be present in the form of geometrical isomers such as cis and trans and optical isomers. These isomers are included in the compounds of the invention.

Further, the compounds of the invention can be in the form of pharmaceutically acceptable salts such as alkali metal salts, e.g., sodium salt and potassium salt.

The processes for preparing the compound of the formula (I) according to the invention are described below.
[Synthetic Process 1]

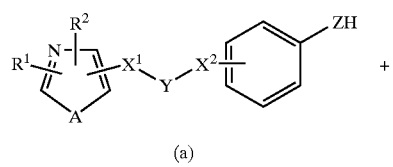

(a)

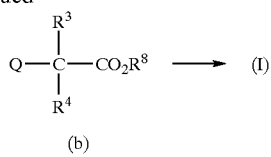

(b)

[in the formulas, Q is a releasing group such as tosyloxy or halogen (e.g., bromine), and $R^1$, $R^2$, $R^3$, $R^4$, $R^8$, A, $X^1$, $X^2$, Y and Z are those described hereinbefore.

In the above-described process, the compound of the formula (I) according to the invention can be prepared by reacting a phenol or thiophenol compound of the general formula (a) with an acetic acid derivative of the general formula (b). The reaction can be carried out in a solvent such as methyl ethyl ketone in the presence of a base such as potassium carbonate.

The starting compound, i.e., the phenol or thiophenol compound of the formula (a), can be prepared by a process similar to the below-mentioned synthetic scheme:
[Synthesis Example 1 for Starting Compound]

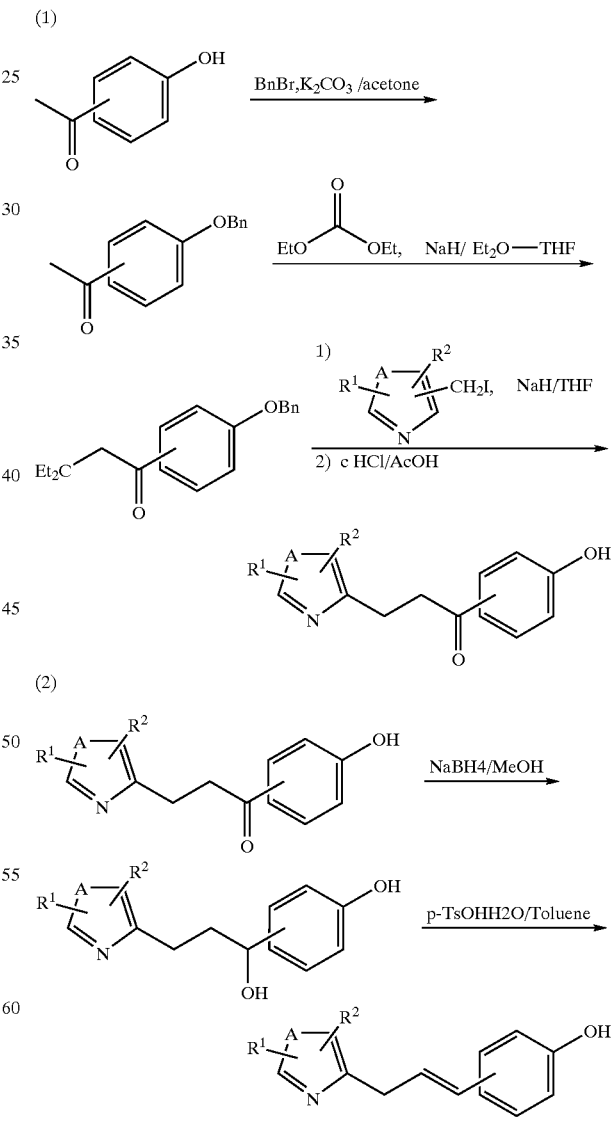

[in the formulas, Bn is benzyl, and $R^1$, $R^2$ and A are those described hereinbefore.]

Further, the following synthetic schemes 2 and 3 can be utilized:

[Synthesis Example 2 for Starting Compound]

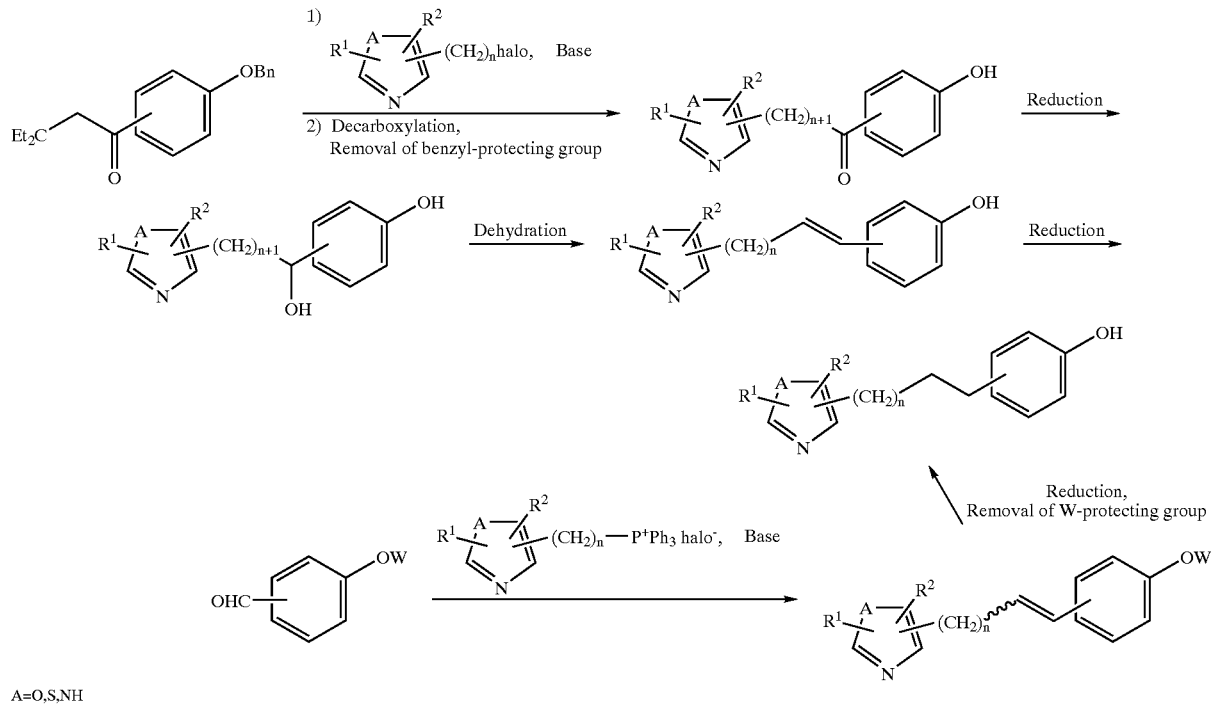

A=O,S,NH

[Synthesis Example 3 for Starting Compound]

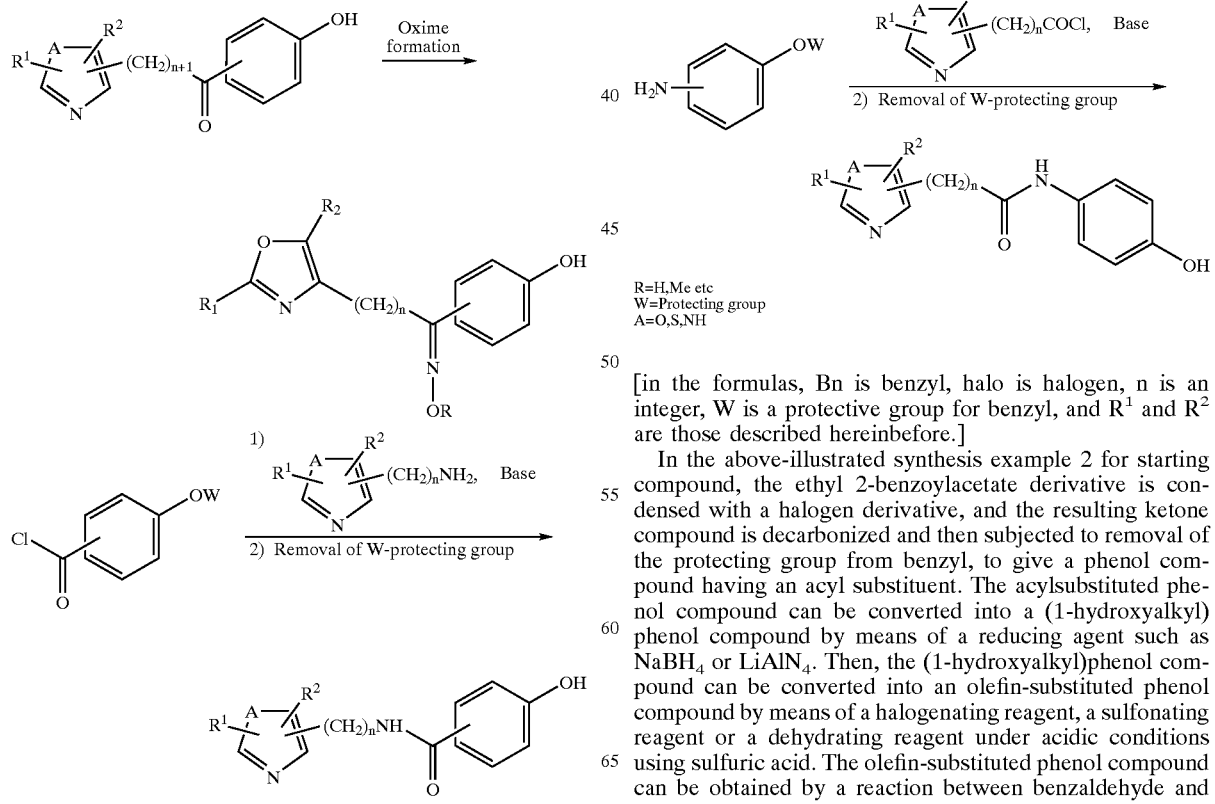

R=H,Me etc
W=Protecting group
A=O,S,NH

[in the formulas, Bn is benzyl, halo is halogen, n is an integer, W is a protective group for benzyl, and $R^1$ and $R^2$ are those described hereinbefore.]

In the above-illustrated synthesis example 2 for starting compound, the ethyl 2-benzoylacetate derivative is condensed with a halogen derivative, and the resulting ketone compound is decarbonized and then subjected to removal of the protecting group from benzyl, to give a phenol compound having an acyl substituent. The acylsubstituted phenol compound can be converted into a (1-hydroxyalkyl) phenol compound by means of a reducing agent such as $NaBH_4$ or $LiAlN_4$. Then, the (1-hydroxyalkyl)phenol compound can be converted into an olefin-substituted phenol compound by means of a halogenating reagent, a sulfonating reagent or a dehydrating reagent under acidic conditions using sulfuric acid. The olefin-substituted phenol compound can be obtained by a reaction between benzaldehyde and Wittig reagent. The olefin-substituted phenol compound can be converted into an alkyl-substituted phenol compound by catalytic reduction in a solvent such as ethanol in the presence of a catalyst such as Pd—C.

Further, the acyl-substituted phenol compound can be converted into an oxime compound utilizing the process illustrated in the synthesis example 3 for starting compound. Furthermore, a carbamoyl-substituted phenol compound can be obtained by the reaction with an amine and a benzoic chloride derivative (if required, a protective group is removed). An acylamino-substituted phenol compound is also obtained by the reaction with an acyl chloride and aniline (if required, a protective group is removed).

[Synthetic Process 2]

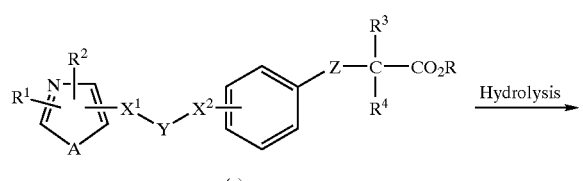

(c)

(d)

[in the formulas, R is $C_{1-6}$ alkyl such as methyl or ethyl, and $R^{11}$, $R^2$, $R^3$, $R^4$, A, $X^1$, $X^2$, Y and Z are those described hereinbefore].

In the above-illustrated process for preparation, a compound of the formula (I) ($R^8$=H) according to the invention can be obtained by the ester compound of the formula (c) is hydrolyzed in a solvent such as aqueous ethanol in the presence of a base such as sodium hydroxide, potassium hydroxide or lithium hydroxide.

[Synthetic Process 3]

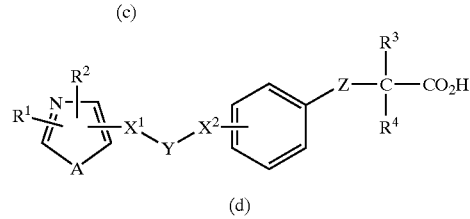

(e)

(f)

[in the formulas, $Y^0$ is a $C_{1-6}$ alkylene chain or a bond, and $R^1$, $R^2$, $R^3$, $R^4$, A, $X^1$ and Z are those described hereinbefore].

In the above-illustrated process, a compound of the formula (I) ($X^2$=bond) according to the invention can be obtained by subjecting the olefin compound of the formula (e) to a reduction reaction in ethanol in the presence of a catalyst such as Pt—C.

[Synthetic Process 4]

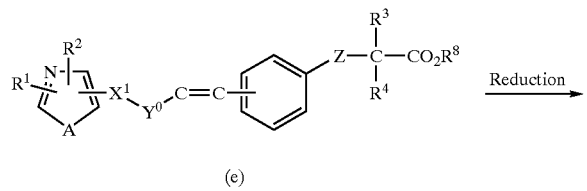

(g)

(h)

[in the formulas, $R^1$, $R^2$, $R^3$, $R^4$, $R^8$, A, $X^1$, Y and Z are those described hereinbefore].

In the above-illustrated process, a compound of the formula (I) ($X^2$=C(=N—OH)) according to the invention can be obtained by reacting the ketone compound of the formula (g) with hydroxylamine.

The representative compounds of the invention are described below.

(1-1) Compounds of the Following Formula (I-a)

Compounds of the formula (I) in which A is O, Z is O, $R^8$ is H, and $X^1$ is attached to the 4-position of the oxazole ring.

TABLE 1

(I-a)

| $R^1$ | $R^2$ | $R^3$ | $R^4$ | $X^1$ | Y | $X^2$ |
|---|---|---|---|---|---|---|
| (2-Cl)phenyl | isopropyl | methyl | methyl | bond | $CH_2CH_2$ | C=O (4) |
| (4-Cl)phenyl | propyl | methyl | methyl | bond | $CH_2CH_2$ | C=O (4) |

TABLE 1-continued

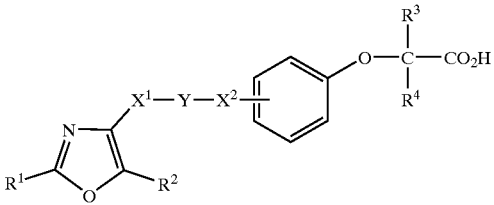

(I-a)

| R¹ | R² | R³ | R⁴ | X¹ | Y | X² |
|---|---|---|---|---|---|---|
| (2-Cl)phenyl | isopropyl | methyl | methyl | bond | CH₂CH₂ | C=O—OH (4) |
| (2-Cl)phenyl | isopropyl | methyl | methyl | bond | CH₂CH₂ | C=(OH) (4) |
| (2-Cl)phenyl | isopropyl | methyl | methyl | bond | CH₂CH₂CH₂ | bond (4) |
| (2-Cl)phenyl | isopropyl | methyl | methyl | bond | CH₂CH₂ | CH=CH (4) |
| phenyl | methyl | methyl | methyl | bond | CH₂CH₂ | C=O (4) |
| 2-pyridyl | ethyl | methyl | methyl | bond | CH₂CH₂ | C=O (4) |
| 2-naphthyl | propyl | methyl | methyl | bond | CH₂CH₂ | bond (4) |
| cyclohexyl | butyl | methyl | methyl | bond | CH₂CH₂ | NHC=O (4) |
| (2-Cl)phenyl | propyl | ethyl | methyl | bond | CH₂CH₂ | CH=CH (4) |
| (2-Cl)phenyl | propyl | methyl | methyl | bond | CH₂CH₂ | C(OH) (4) |
| (2,4-Cl)phenyl | propyl | methyl | methyl | bond | CH₂CH₂ | C=N—OH (4) |
| (2-Bu)phenyl | hexyl | methyl | methyl | bond | CH₂CH₂CH₂ | C=O (4) |
| (4-tBu)phenyl | hexyl | methyl | methyl | O | CH₂CH₂ | O (3) |

Remark: Numeral in ( ) means a position of X².

(1-2) Compounds of the Above-illustrated Formula (I-a)

TABLE 2

| R¹ | R² | R³ | R⁴ | X¹ | Y | X² |
|---|---|---|---|---|---|---|
| (2-Cl)phenyl | t-butyl | ethyl | ethyl | NHCO | CH₂CH₂ | C=O(3) |
| (2-Cl)phenyl | isopropyl | methyl | methyl | CONH | CH₂CH₂ | C=O(3) |
| (2,3-F)phenyl | isobutyl | methyl | methyl | bond | CH₂CH₂ | C=O(3) |
| (2,4-F)phenyl | trifluoromethyl | methyl | methyl | bond | CH₂CH₂ | NHC=O(3) |
| (2,3-F)phenyl | trifluoroethyl | methyl | methyl | bond | CH₂CH₂ | CH=CH(3) |
| (2,4-F)phenyl | difluoroethyl | methyl | methyl | bond | CH₂CH₂ | C(OMe)(3) |
| (2-CF₃)phenyl | isopropyl | methyl | methyl | bond | CH₂CH₂ | C=O(4) |
| (2,6-Cl)phenyl | isopropyl | difluoromethyl | methyl | bond | CH₂CH₂ | C=O(4) |
| (2-Cl)phenyl | cyclopropyl | fluoromethyl | methyl | bond | CH=CH | C=O(4) |
| (2,3-F)phenyl | 2-propenyl | methyl | methyl | bond | CH₂ | C=O(4) |
| (2,3-Cl)phenyl | vinyl | methyl | methyl | bond | CH₂CH=CH | C=O(4) |
| (2,3-Cl)phenyl | 2-propenyl | methyl | methyl | bond | CH₂ | C=O(4) |
| (2,4-F)phenyl | propargyl | methyl | methyl | bond | CH₂ | C=ONH(4) |
| hexyl | cyclopropylmethyl | methyl | methyl | bond | CH₂CH₂CH₂ | C=O(3) |
| 2-quinolyl | isopropyl | methyl | methyl | bond | CH₂CH₂CH₂ | bond(3) |
| (2-Cl)phenyl | propyl | methyl | methyl | bond | CH₂CH₂ | C(OH)(4) |
| (2-Cl)phenyl | isopropyl | ethyl | methyl | bond | CH₂ | CH=CH(3) |
| (2-OMe)phenyl | isopropyl | ethyl | methyl | bond | CH₂CH₂ | NHCO(4) |
| (2-Me)phenyl | isopropyl | methyl | methyl | bond | CH₂CH₂CH₂ | C=O(4) |
| (4-Cl)phenyl | isopropyl | methyl | methyl | bond | CH₂CH₂ | C=O(4) |

Remark: Numeral in ( ) means a position of X².

(2) Compounds of the Following Formula (I-b)

Compounds of the formula (I) in which A is O, Z is S, $R^8$ is H, and $X^1$ is attached to the 4-position of the oxazole ring.

TABLE 3

(I-b)

| $R^1$ | $R^2$ | $R^3$ | $R^4$ | $X^1$ | Y | $X^2$ |
|---|---|---|---|---|---|---|
| (2-Cl)phenyl | isopropyl | methyl | methyl | bond | $CH_2CH_2$ | C=O (4) |
| (4-Cl)phenyl | propyl | methyl | methyl | bond | $CH_2CH_2$ | C=O (4) |
| (2-Cl)phenyl | isopropyl | methyl | methyl | bond | $CH_2CH_2$ | C=N—OH (4) |
| (2-Cl)phenyl | isopropyl | methyl | methyl | bond | $CH_2CH_2$ | CH(OH) (4) |
| (2-Cl)phenyl | isopropyl | methyl | methyl | bond | $CH_2CH_2CH_2$ | bond (4) |
| (2-Cl)phenyl | isopropyl | methyl | methyl | bond | $CH_2CH_2$ | CH=CH (4) |
| phenyl | methyl | methyl | methyl | bond | $CH_2CH_2$ | C=O (4) |
| 2-pyridyl | ethyl | methyl | methyl | bond | $CH_2CH_2$ | C=O (4) |
| 2-naphthyl | propyl | methyl | methyl | bond | $CH_2CH_2CH_2$ | bond (4) |
| cyclohexyl | butyl | methyl | methyl | bond | $CH_2CH_2$ | NHC=O (4) |
| (2-Cl)phenyl | propyl | ethyl | methyl | bond | $CH_2$ | CH=CH (4) |
| (2-Cl)phenyl | propyl | methyl | methyl | bond | $CH_2CH_2$ | CH(OH) (4) |
| (2,4-Cl)phenyl | propyl | methyl | methyl | bond | $CH_2CH_2$ | C=N—OH (4) |

Remark: Numeral in ( ) means a position of $X^2$.

(3-1) Compounds of the Following Formula (I-c)

Compounds of the formula (I) in which A is not O, each of $R^3$ and $R^4$ is methyl, Z is O, $R^8$ is H, and $X^1$ is attached, for example, to the 4-position of the thiazole ring.

TABLE 4

(I-c)

| $R^1$ | $R^2$ | A | $X^1$ | Y | $X^2$ |
|---|---|---|---|---|---|
| (2-Cl)phenyl | isopropyl | S | bond | $CH_2CH_2$ | C=O (4) |
| (4-Cl)phenyl | propyl | S | bond | $CH_2CH_2$ | C=O (4) |
| (2-Cl)phenyl | isopropyl | NH | bond | $CH_2CH_2$ | C=N—OH (4) |
| (2-Cl)phenyl | isopropyl | N—Me | bond | $CH_2CH_2$ | CH(OH) (4) |
| (2-Cl)phenyl | isopropyl | N—Et | bond | $CH_2CH_2CH_2$ | bond (4) |
| (2-Cl)phenyl | isopropyl | N—Bn | bond | $CH_2CH_2$ | CH=CH (4) |
| phenyl | methyl | S | bond | $CH_2CH_2$ | C=O (4) |
| 2-pyridyl | ethyl | S | bond | $CH_2CH_2$ | C=O (4) |
| 2-naphthyl | propyl | NH | bond | $CH_2CH_2$ | bond (4) |
| cyclohexyl | butyl | N—Me | bond | $CH_2CH_2$ | NHC=O (4) |
| (2-Cl)phenyl | propyl | N—Et | bond | $CH_2CH_2$ | CH=CH (4) |
| (2-Cl)phenyl | propyl | N—Bn | bond | $CH_2CH_2$ | CH(OH) (4) |
| (2,4-Cl)phenyl | propyl | S | bond | $CH_2CH_2$ | C=N—OH (4) |
| (4-Bu)phenyl | hexyl | NH | bond | $CH_2CH_2CH_2$ | C=O (4) |
| (4-tBu)phenyl | hexyl | N—Me | O | $CH_2CH_2$ | O (3) |
| (2-Cl)phenyl | t-butyl | N—Et | NHCO | $CH_2CH_2$ | C=O (3) |

Remark: Numeral in ( ) means a position of $X^2$.

(3-2) Compounds of the Above-illustrated Formula (I-c)

TABLE 5

| $R^1$ | $R^2$ | A | $X^1$ | Y | $X^2$ |
|---|---|---|---|---|---|
| (2-Cl)phenyl | isopropyl | N—Bn | CONH | $CH_2CH_2$ | C=O(3) |
| (2,3-F)phenyl | isobutyl | S | bond | $CH_2CH_2$ | C=O(3) |
| (2,4-F)phenyl | trifluoro-methyl | S | bond | $CH_2CH_2$ | NHC=O(3) |
| (2,3-F)phenyl | trifluoro-ethyl | NH | bond | $CH_2CH_2$ | CH=CH(4) |
| (2,4-F)phenyl | difluoro-ethyl | N—Me | bond | $CH_2CH_2$ | C(OMe)(3) |
| (2-$CF_3$)phenyl | isopropyl | N—Et | bond | $CH_2CH_2$ | C=O(4) |
| (2,6-Cl)phenyl | isopropyl | N—Bn | bond | $CH_2CH_2$ | C=O(4) |
| (2-Cl)phenyl | cyclopropyl | S | bond | CH=CH | C=O(4) |
| (2,3-F)phenyl | 2-propenyl | S | bond | $CH_2$ | C=O(4) |
| (2,3-Cl)phenyl | vinyl | NH | bond | $CH_2CH$=CH | C=O(4) |
| (2,3-Cl)phenyl | 2-propenyl | N—Me | bond | $CH_2$ | C=O(4) |
| (2,4-F)phenyl | propargyl | N—Et | bond | $CH_2$ | C=ONH(3) |
| hexyl | cyclopropyl-methyl | N—Bn | bond | $CH_2CH_2CH_2$ | C=O(3) |
| 2-quinolyl | isopropyl | S | bond | $CH_2CH_2CH_2$ | bond(3) |
| (2-Cl)phenyl | isopropyl | S | bond | $CH_2$ | CH=CH(3) |
| (2-OMe)phenyl | isopropyl | S | bond | $CH_2CH_2$ | NHCO(3) |
| (2-OMe)phenyl | isopropyl | S | bond | $CH_2CH_2CH_2$ | C=O(4) |
| (4-Cl)phenyl | isopropyl | S | bond | $CH_2CH_2$ | C=O(4) |

Remark: Numeral in ( ) means a position of $X^2$.

(4-1) Compounds of the Following Formula (I-d)

Compounds of the formula (I) in which each of $R^3$ and $R^4$ is methyl, Z is O, $R^8$ is H, and $X^1$ is attached, for example, to the 2-position of the thiazole ring.

TABLE 6

(I-d)

[Structure: thiazole ring with $R^1$ and $R^2$ substituents and A, connected via $X^1$—Y—$X^2$ to a phenyl group bearing O—C(Me)(Me)—$CO_2H$]

| $R^1$ | $R^2$ | A | $X^1$ | Y | $X^2$ |
|---|---|---|---|---|---|
| (2-Cl)phenyl | isopropyl | O | bond | $CH_2CH_2$ | C=O (4) |
| (4-Cl)phenyl | propyl | O | bond | $CH_2CH_2$ | C=O (4) |
| (2-Cl)phenyl | isopropyl | O | bond | $CH_2CH_2$ | C=N—OH (4) |
| (2-Cl)phenyl | isopropyl | O | bond | $CH_2CH_2$ | CH(OH) (4) |
| (2-Cl)phenyl | isopropyl | O | bond | $CH_2CH_2CH_2$ | bond (4) |
| (2-Cl)phenyl | isopropyl | O | bond | $CH_2CH_2$ | CH=CH (4) |
| phenyl | methyl | S | bond | $CH_2CH_2$ | C=O (4) |
| 2-pyridyl | ethyl | S | bond | $CH_2CH_2$ | C=O (4) |
| 2-naphthyl | propyl | O | bond | $CH_2CH_2$ | bond (4) |
| cyclohexyl | butyl | O | bond | $CH_2CH_2$ | NHC=O (4) |
| (2-Cl)phenyl | propyl | O | bond | $CH_2CH_2$ | CH=CH (4) |
| (2-Cl)phenyl | propyl | O | bond | $CH_2CH_2$ | CH(OH) (4) |
| (2,4-Cl)phenyl | propyl | O | bond | $CH_2CH_2$ | C=N—OH (4) |
| (4-Bu)phenyl | hexyl | S | bond | $CH_2CH_2CH_2$ | C=O (4) |
| (4-tBu)phenyl | hexyl | N—Me | bond | $CH_2CH_2CH_2$ | O (3) |
| (2-Cl)phenyl | t-butyl | N—Et | NHCO | $CH_2CH_2$ | C=O (3) |

Remark: Numeral in ( ) means a position of $X^2$.

(4-2) Compounds of the Above-illustrated Formula (I-d)

TABLE 7

| $R^1$ | $R^2$ | A | $X^1$ | Y | $X^2$ |
|---|---|---|---|---|---|
| (2-Cl)phenyl | isopropyl | N—Bn | CONH | $CH_2CH_2$ | C=O(3) |
| (2,3-F)phenyl | isobutyl | O | bond | $CH_2CH_2$ | C=O(3) |
| (2,4-F)phenyl | trifluoro-methyl | O | bond | $CH_2CH_2$ | NHC=O(3) |
| (2,3-F)phenyl | trifluoro-ethyl | O | bond | $CH_2CH_2$ | CH=CH(3) |
| (2,4-F)phenyl | difluoro-ethyl | O | bond | $CH_2CH_2$ | C(OMe)(3) |
| (2-$CF_3$)phenyl | isopropyl | O | bond | $CH_2CH_2$ | C=O(4) |
| (2,4-Cl)phenyl | isopropyl | O | bond | $CH_2CH_2$ | C=O(4) |
| (2-Cl)phenyl | cyclopropyl | O | bond | CH=CH | C=O(4) |
| (2,3-F)phenyl | 2-propenyl | S | bond | $CH_2$ | C=O(4) |
| (2,3-Cl)phenyl | vinyl | NH | bond | $CH_2CH=CH$ | C=O(4) |
| (2,3-Cl)phenyl | 2-propenyl | N—Me | bond | $CH_2$ | C=O(4) |
| (2,4-F)phenyl | propargyl | N—Et | bond | $CH_2$ | C=ONH(3) |
| hexyl | cyclopropyl- | N—Bn | bond | $CH_2CH_2CH_2$ | C=O(3) |
| 2-quinolyl | isopropyl | S | bond | $CH_2CH_2CH_2$ | bond(3) |
| (2-Cl)phenyl | isopropyl | S | bond | $CH_2$ | CH=CH(3) |
| (2-OMe)phenyl | isopropyl | S | bond | $CH_2CH_2$ | NHCO(3) |
| (2-Me)phenyl | isopropyl | S | bond | $CH_2CH_2CH_2$ | C=O(4) |
| (4-Cl)phenyl | isopropyl | S | bond | $CH_2CH_2CH_2$ | C=O(4) |

Remark: Numeral in ( ) means a position of $X^2$.

(5-1) Compounds of the Following Formula (I-e)
Compounds of the formula (I) in which each of $R^3$ and $R^4$ is methyl, Z is O, $R^8$ is H, and $X^1$ is attached, for example, to the 5-position of the thiazole ring.

TABLE 8

(I-e)

| $R^1$ | $R^2$ | A | $X^1$ | Y | $X^2$ |
|---|---|---|---|---|---|
| (2-Cl)phenyl | isopropyl | S | bond | $CH_2CH_2$ | C=O (4) |
| (4-Cl)phenyl | propyl | S | bond | $CH_2CH_2$ | C=O (4) |
| (2-Cl)phenyl | isopropyl | NH | bond | $CH_2CH_2$ | C=N—OH (4) |
| (2-Cl)phenyl | isopropyl | N—Me | bond | $CH_2CH_2$ | CH(OH) (4) |
| (2-Cl)phenyl | isopropyl | N—Et | bond | $CH_2CH_2CH_2$ | bond (4) |
| (2-Cl)phenyl | isopropyl | N—Bn | bond | $CH_2CH_2$ | CH=CH (4) |
| phenyl | methyl | S | bond | $CH_2CH_2$ | C=O (4) |
| 2-pyridyl | ethyl | S | bond | $CH_2CH_2$ | C=O (4) |
| 2-naphthyl | propyl | NH | bond | $CH_2CH_2$ | bond (4) |
| cyclohexyl | butyl | N—Me | bond | $CH_2CH_2$ | NHC=O (4) |
| (2-Cl)phenyl | propyl | N—Et | bond | $CH_2CH_2$ | CH=CH (4) |
| (2-Cl)phenyl | propyl | N—Bn | bond | $CH_2CH_2$ | CH(OH) (4) |
| (2,4-Cl)phenyl | propyl | S | bond | $CH_2CH_2$ | C=N—OH (4) |
| (4-Bu)phenyl | hexyl | NH | bond | $CH_2CH_2CH_2$ | C=O (4) |
| (4-tBu)phenyl | hexyl | N—Me | O | $CH_2CH_2$ | O (3) |
| (2-Cl)phenyl | t-butyl | N—Et | NHCO | $CH_2CH_2$ | C=O (3) |

Remark: Numeral in ( ) means a position of $X^2$.

(5-2) Compounds of the Above-illustrated Formula (I-e)

TABLE 9

| R¹ | R² | A | X¹ | Y | X² |
|---|---|---|---|---|---|
| (2-Cl)phenyl | isopropyl | N—Bn | CONH | $CH_2CH_2$ | C=O(3) |
| (2,3-F)phenyl | isobutyl | S | bond | $CH_2CH_2$ | C=O(3) |
| (2,4-F)phenyl | trifluoromethyl | S | bond | $CH_2CH_2$ | NHC=O(3) |
| (2,3-F)phenyl | trifluoroethyl | NH | bond | $CH_2CH_2$ | CH=CH(3) |
| (2,4-F)phenyl | difluoroethyl | N—Me | bond | $CH_2CH_2$ | C(OMe)(3) |
| (2-CF₃)phenyl | isopropyl | N—Et | bond | $CH_2CH_2$ | C=O(4) |
| (2,6-Cl)phenyl | isopropyl | N—Bn | bond | $CH_2CH_2$ | C=O(4) |
| (2-Cl)phenyl | cyclopropyl | S | bond | CH=CH | C=O(4) |
| (2,3-F)phenyl | 2-propenyl | S | bond | $CH_2$ | C=O(4) |
| (2,3-Cl)phenyl | vinyl | NH | bond | $CH_2CH=CH$ | C=O(4) |
| (2,3-Cl)phenyl | 2-propenyl | N—Me | bond | $CH_2$ | C=O(4) |
| (2,4-F)phenyl | propargyl | N—Et | bond | $CH_2$ | C=ONH(3) |
| hexyl | cyclopropylmethyl | N—Bn | bond | $CH_2CH_2CH_2$ | C=O(3) |
| 2-quinolyl | isopropyl | S | bond | $CH_2CH_2CH_2$ | bond(3) |
| (2-Cl)phenyl | isopropyl | S | bond | $CH_2$ | CH=CH(3) |
| (2-OMe)phenyl | isopropyl | S | bond | $CH_2CH_2$ | NHCO(3) |
| (2-OMe)phenyl | isopropyl | S | bond | $CH_2CH_2CH_2$ | C=O(4) |
| (4-Cl)phenyl | isopropyl | S | bond | $CH_2CH_2$ | C=O(4) |

Remark: Numeral in ( ) means a position of $X^2$.

(6) Oxazole Derivatives of the Following Formula:

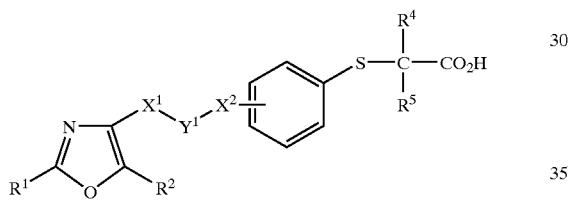

[in the formula, $R^1$, $R^2$, $R^4$, $R^5$, $X^1$, $X^2$ and $Y^1$ are those described in Tables 10 to 15].

TABLE 10

| R¹ | R² | R⁴ | R⁵ | X¹ | Y¹ | X² |
|---|---|---|---|---|---|---|
| (2-Cl)phenyl | isopropyl | methyl | methyl | bond | $CH_2NH$ | C=O(4) |
| (2-Cl)phenyl | isopropyl | methyl | methyl | bond | $CH_2C=O$ | NH(4) |
| (2-Cl)phenyl | isopropyl | methyl | methyl | bond | $CH_2CH_2CH_2$ | C=O(4) |
| (2,4-Cl)phenyl | isopropyl | methyl | methyl | bond | $CH_2CH_2$ | C=O(4) |
| (2,4-Cl)phenyl | isopropyl | methyl | ethyl | bond | $CH_2CH_2$ | C=O(4) |
| (3,4-Cl)phenyl | isopropyl | methyl | methyl | bond | $CH_2CH_2$ | C=O(4) |
| 2-benzofuranyl | isopropyl | methyl | methyl | bond | $CH_2CH_2$ | C=O(4) |
| 4-biphenylyl | isopropyl | methyl | methyl | bond | $CH_2CH_2$ | C=O(4) |
| 1-OH-2-naphthyl | isopropyl | methyl | methyl | bond | $CH_2CH_2$ | C=O(4) |
| (2,4-Cl)phenyl | isopropyl | methyl | methyl | bond | $CH_2$ | C=O(4) |
| 3-OH-2-naphthyl | isopropyl | methyl | methyl | bond | $CH_2CH_2$ | C=O(4) |
| (2-OH,4-Cl)-phenyl | isopropyl | methyl | methyl | bond | $CH_2CH_2$ | C=O(4) |
| (2-Cl,4-Br)-phenyl | isopropyl | methyl | methyl | bond | $CH_2CH_2$ | C=O(4) |
| 3-Cl-4-biphenylyl | isopropyl | methyl | methyl | bond | $CH_2CH_2$ | C=O(4) |
| (2-OH,4-Me)-phenyl | isopropyl | methyl | methyl | bond | $CH_2CH_2$ | C=O(4) |
| (2,4-Me)phenyl | isopropyl | methyl | methyl | bond | $CH_2CH_2$ | C=O(4) |
| (2-OH)phenyl | isopropyl | methyl | methyl | bond | $CH_2CH_2$ | C=O(4) |
| (2-OH,3,4-Me)-phenyl | isopropyl | methyl | methyl | bond | $CH_2CH_2$ | C=O(4) |

TABLE 10-continued

| R¹ | R² | R⁴ | R⁵ | X¹ | Y¹ | X² |
|---|---|---|---|---|---|---|
| (2-OH,4-CF₃)-phenyl | isopropyl | methyl | methyl | bond | CH₂CH₂ | C=O(4) |
| (2-Cl,4-OMe)-phenyl | isopropyl | methyl | methyl | bond | CH₂CH₂ | C=O(4) |

Remark: Numeral in ( ) means a position of X².

TABLE 11

| R¹ | R² | R⁴ | R⁵ | X¹ | Y¹ | X² |
|---|---|---|---|---|---|---|
| (2-Cl,4-OPh)-phenyl | isopropyl | methyl | methyl | bond | CH₂CH₂ | C=O(4) |
| 1-naphthyl | isopropyl | methyl | methyl | bond | CH₂CH₂ | C=O(4) |
| 2-naphthyl | isopropyl | methyl | methyl | bond | CH₂CH₂ | C=O(4) |
| 2-quinolyl | isopropyl | methyl | methyl | bond | CH₂CH₂ | C=O(4) |
| 8-quinolyl | isopropyl | methyl | methyl | bond | CH₂CH₂ | C=O(4) |
| 3-quinolyl | isopropyl | methyl | methyl | bond | CH₂CH₂ | C=O(4) |
| 2-pyrimidyl | isopropyl | methyl | methyl | bond | CH₂CH₂ | C=O(4) |
| 2-thienyl | isopropyl | methyl | methyl | bond | CH₂CH₂ | C=O(4) |
| 2-furanyl | isopropyl | methyl | methyl | bond | CH₂CH₂ | C=O(4) |
| 2-imidazolyl | isopropyl | methyl | methyl | bond | CH₂CH₂ | C=O(4) |
| 2-indolyl | isopropyl | methyl | methyl | bond | CH₂CH₂ | C=O(4) |
| 2-benzothienyl | isopropyl | methyl | methyl | bond | CH₂CH₂ | C=O(4) |
| 2-benzimidazolyl | isopropyl | methyl | methyl | bond | CH₂CH₂ | C=O(4) |
| (2-OH,4-Me)phenyl | propyl | methyl | methyl | bond | CH₂CH₂ | C=O(4) |
| (2,4-Me)phenyl | propyl | methyl | methyl | bond | CH₂CH₂ | C=O(4) |
| (2-OH)phenyl | propyl | methyl | methyl | bond | CH₂CH₂ | C=O(4) |
| (2-OH,3,4-Me)-phenyl | propyl | methyl | methyl | bond | CH₂CH₂ | C=O(4) |
| (2-OH,4-CF₃)-phenyl | propyl | methyl | methyl | bond | CH₂CH₂ | C=O(4) |
| (2-Cl,4-OMe)phenyl | propyl | methyl | methyl | bond | CH₂CH₂ | C=O(4) |
| (2-Cl,4-OPh)phenyl | propyl | methyl | methyl | bond | CH₂CH₂ | C=O(4) |

Remark: Numeral in ( ) means a position of X².

TABLE 12

| R¹ | R² | R⁴ | R⁵ | X¹ | Y¹ | X² |
|---|---|---|---|---|---|---|
| 1-naphthyl | propyl | methyl | methyl | bond | CH₂CH₂ | C=O(4) |
| 2-naphthyl | propyl | methyl | methyl | bond | CH₂CH₂ | C=O(4) |
| 2-quinolyl | propyl | methyl | methyl | bond | CH₂CH₂ | C=O(4) |
| 8-quinolyl | propyl | methyl | methyl | bond | CH₂CH₂ | C=O(4) |
| 3-quinolyl | propyl | methyl | methyl | bond | CH₂CH₂ | C=O(4) |
| 2-pyrimidyl | propyl | methyl | methyl | bond | CH₂CH₂ | C=O(4) |
| 2-thienyl | propyl | methyl | methyl | bond | CH₂CH₂ | C=O(4) |
| 2-furanyl | propyl | methyl | methyl | bond | CH₂CH₂ | C=O(4) |
| 2-imidazolyl | propyl | methyl | methyl | bond | CH₂CH₂ | C=O(4) |
| 2-indolyl | propyl | methyl | methyl | bond | CH₂CH₂ | C=O(4) |
| 2-benzothienyl | propyl | methyl | methyl | bond | CH₂CH₂ | C=O(4) |
| 2-benzimidazolyl | propyl | methyl | methyl | bond | CH₂CH₂ | C=O(4) |
| (2-Cl)phenyl | isopropyl | methyl | methyl | bond | CH₂NH | C=O(4) |
| (4-Cl)phenyl | isopropyl | methyl | methyl | bond | CH₂C=O | NH(3) |
| (2-Cl)phenyl | isopropyl | methyl | methyl | bond | CH₂CH₂CH₂ | C=O(3) |
| (2,4-Cl)phenyl | isopropyl | methyl | methyl | bond | CH₂CH₂ | C=O(3) |
| (2,4-Cl)phenyl | isopropyl | methyl | ethyl | bond | CH₂CH₂ | C=O(3) |
| (3,4-Cl)phenyl | isopropyl | methyl | methyl | bond | CH₂CH₂ | C=O(3) |
| 2-benzofuranyl | propyl | methyl | methyl | bond | CH₂CH₂ | C=O(3) |
| 4-biphenylyl | propyl | methyl | methyl | bond | CH₂CH₂ | C=O(3) |

Remark: Numeral in ( ) means a position of X².

TABLE 13

| R¹ | R² | R⁴ | R⁵ | X¹ | Y¹ | X² |
|---|---|---|---|---|---|---|
| 1-OH-2-naphthyl | isopropyl | methyl | methyl | bond | CH₂CH₂ | C=O(3) |
| (2,4-Cl)phenyl | isopropyl | methyl | methyl | bond | CH₂CH₂ | CH=CH(3) |
| 3-OH-2-naphthyl | isopropyl | methyl | methyl | bond | CH₂CH₂ | C=O(3) |
| (2-OH,4-Cl)-phenyl | isopropyl | methyl | methyl | bond | CH₂CH₂ | C=O(3) |

TABLE 13-continued

| R¹ | R² | R⁴ | R⁵ | X¹ | Y¹ | X² |
|---|---|---|---|---|---|---|
| (2-Cl,4-Br)-phenyl | isopropyl | methyl | methyl | bond | CH₂CH₂ | C=O(3) |
| 3-Cl-4-biphenylyl | isopropyl | methyl | methyl | bond | CH₂CH₂ | C=O(3) |
| (2-OH,4-Me)-phenyl | isopropyl | methyl | methyl | bond | CH₂CH₂ | C=O(3) |
| (2,4-Me)phenyl | isopropyl | methyl | methyl | bond | CH₂CH₂ | C=O(3) |
| (2-OH)phenyl | isopropyl | methyl | methyl | bond | CH₂CH₂ | C=O(3) |
| (2-OH,3,4-Me)-phenyl | isopropyl | methyl | methyl | bond | CH₂CH₂ | C=O(3) |
| (2-OH,4-CF₃)-phenyl | isopropyl | methyl | methyl | bond | CH₂CH₂ | C=O(3) |
| (2-Cl,4-OMe)-phenyl | isopropyl | methyl | methyl | bond | CH₂CH₂ | C=O(3) |
| (2-Cl,4-OPh)-phenyl | isopropyl | methyl | methyl | bond | CH₂CH₂ | C=O(3) |
| 1-naphthyl | isopropyl | methyl | methyl | bond | CH₂CH₂ | C=O(3) |
| 2-naphthyl | isopropyl | methyl | methyl | bond | CH₂CH₂ | C=O(3) |
| 2-quinolyl | isopropyl | methyl | methyl | bond | CH₂CH₂ | C=O(3) |
| 8-quinolyl | isopropyl | methyl | methyl | bond | CH₂CH₂ | C=O(3) |
| 3-quinolyl | isopropyl | methyl | methyl | bond | CH₂CH₂ | C=O(3) |
| 2-pyrimidyl | isopropyl | methyl | methyl | bond | CH₂CH₂ | C=O(3) |

Remark: Numeral in ( ) means a position of X².

TABLE 14

| R¹ | R² | R⁴ | R⁵ | X¹ | Y¹ | X² |
|---|---|---|---|---|---|---|
| 2-furanyl | isopropyl | methyl | methyl | bond | CH₂CH₂ | C=O(3) |
| 2-imidazolyl | isopropyl | methyl | methyl | bond | CH₂CH₂ | C=O(3) |
| 2-indolyl | isopropyl | methyl | methyl | bond | CH₂CH₂ | C=O(3) |
| 2-benzothienyl | isopropyl | methyl | methyl | bond | CH₂CH₂ | C=O(3) |
| 2-benzimidazolyl | isopropyl | methyl | methyl | bond | CH₂CH₂ | C=O(3) |
| (2-OH,4-Me)phenyl | propyl | methyl | methyl | bond | CH₂CH₂ | C=O(3) |
| (2,4-Me)phenyl | propyl | methyl | methyl | bond | CH₂CH₂ | C=O(3) |
| (2-OH)phenyl | propyl | methyl | methyl | bond | CH₂CH₂ | C=O(3) |
| (2-OH,3,4-Me)-phenyl | propyl | methyl | methyl | bond | CH₂CH₂ | C=O(3) |
| (2-OH,4-CF₃)-phenyl | propyl | methyl | methyl | bond | CH₂CH₂ | C=O(3) |
| (2-Cl,4-OMe)-phenyl | propyl | methyl | methyl | bond | CH₂CH₂ | C=O(3) |
| (2-Cl,4-OPh)-phenyl | propyl | methyl | methyl | bond | CH₂CH₂ | C=O(3) |
| 1-naphthyl | propyl | methyl | methyl | bond | CH₂CH₂ | C=O(3) |
| 2-naphthyl | propyl | methyl | methyl | bond | CH₂CH₂ | C=O(3) |
| 2-quinolyl | propyl | methyl | methyl | bond | CH₂CH₂ | C=O(3) |
| 8-quinolyl | propyl | methyl | methyl | bond | CH₂CH₂ | C=O(3) |
| 3-quinolyl | propyl | methyl | methyl | bond | CH₂CH₂ | C=O(3) |
| 2-pyrimidyl | propyl | methyl | methyl | bond | CH₂CH₂ | C=O(3) |
| 2-thienyl | propyl | methyl | methyl | bond | CH₂CH₂ | C=O(3) |
| 2-furanyl | propyl | methyl | methyl | bond | CH₂CH₂ | C=O(3) |

Remark: Numeral in ( ) means a position of X².

TABLE 15

| R¹ | R² | R⁴ | R⁵ | X¹ | Y¹ | X² |
|---|---|---|---|---|---|---|
| 2-imidazolyl | propyl | methyl | methyl | bond | CH₂CH₂ | C=O(3) |
| 2-indolyl | propyl | methyl | methyl | bond | CH₂CH₂ | C=O(3) |
| 2-benzothienyl | propyl | methyl | methyl | bond | CH₂CH₂ | C=O(3) |
| 2-benzimidazolyl | propyl | methyl | methyl | bond | CH₂CH₂ | C=O(3) |

Remark: Numeral in ( ) means a position of X².

(7) Oxazole Derivatives of the Following Formula:

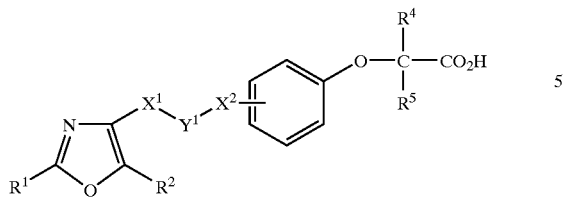

[in the formula, $R^1$, $R^2$, $R^4$, $R^5$, $X^1$, $X^2$ and $Y^1$ are those described in Tables 16 to 21].

TABLE 16

| $R^1$ | $R^2$ | $R^4$ | $R^5$ | $X^1$ | $Y^1$ | $X^2$ |
|---|---|---|---|---|---|---|
| (2-Cl)phenyl | isopropyl | methyl | methyl | bond | CH$_2$NH | C=O(4) |
| (2-Cl)phenyl | isopropyl | methyl | methyl | bond | CH$_2$C=O | NH(4) |
| (2-Cl)phenyl | isopropyl | methyl | methyl | bond | CH$_2$CH$_2$CH$_2$ | C=O(4) |
| (2,4-Cl)phenyl | isopropyl | methyl | methyl | bond | CH$_2$CH$_2$ | C=O(4) |
| (2,4-Cl)phenyl | isopropyl | methyl | ethyl | bond | CH$_2$CH$_2$ | C=O(4) |
| (3,4-Cl)phenyl | isopropyl | methyl | methyl | bond | CH$_2$CH$_2$ | C=O(4) |
| 2-benzofuranyl | isopropyl | methyl | methyl | bond | CH$_2$CH$_2$ | C=O(4) |
| 4-biphenylyl | isopropyl | methyl | methyl | bond | CH$_2$CH$_2$ | C=O(4) |
| 1-OH-2-naphthyl | isopropyl | methyl | methyl | bond | CH$_2$CH$_2$ | C=O(4) |
| (2,4-Cl)phenyl | isopropyl | methyl | methyl | bond | CH$_2$ | C=O(4) |
| 3-OH-2-naphthyl | isopropyl | methyl | methyl | bond | CH$_2$CH$_2$ | C=O(4) |
| (2-OH,4-Cl)-phenyl | isopropyl | methyl | methyl | bond | CH$_2$CH$_2$ | C=O(4) |
| (2-Cl,4-Br)-phenyl | isopropyl | methyl | methyl | bond | CH$_2$CH$_2$ | C=O(4) |
| 3-Cl-4-biphenylyl | isopropyl | methyl | methyl | bond | CH$_2$CH$_2$ | C=O(4) |
| (2-OH,4-Me)-phenyl | isopropyl | methyl | methyl | bond | CH$_2$CH$_2$ | C=O(4) |
| (2,4-Me)phenyl | isopropyl | methyl | methyl | bond | CH$_2$CH$_2$ | C=O(4) |
| (2-OH)phenyl | isopropyl | methyl | methyl | bond | CH$_2$CH$_2$ | C=O(4) |
| (2-OH,3,4-Me)-phenyl | isopropyl | methyl | methyl | bond | CH$_2$CH$_2$ | C=O(4) |
| (2-OH,4-CF$_3$)-phenyl | isopropyl | methyl | methyl | bond | CH$_2$CH$_2$ | C=O(4) |
| (2-Cl,4-OMe)-phenyl | isopropyl | methyl | methyl | bond | CH$_2$CH$_2$ | C=O(4) |

Remark: Numeral in ( ) means a position of $X^2$.

TABLE 17

| $R^1$ | $R^2$ | $R^4$ | $R^5$ | $X^1$ | $Y^1$ | $X^2$ |
|---|---|---|---|---|---|---|
| (2-Cl,4-OPh)-phenyl | isopropyl | methyl | methyl | bond | CH$_2$CH$_2$ | C=O(4) |
| 1-naphthyl | isopropyl | methyl | methyl | bond | CH$_2$CH$_2$ | C=O(4) |
| 2-naphthyl | isopropyl | methyl | methyl | bond | CH$_2$CH$_2$ | C=O(4) |
| 2-quinolyl | isopropyl | methyl | methyl | bond | CH$_2$CH$_2$ | C=O(4) |
| 8-quinolyl | isopropyl | methyl | methyl | bond | CH$_2$CH$_2$ | C=O(4) |
| 3-quinolyl | isopropyl | methyl | methyl | bond | CH$_2$CH$_2$ | C=O(4) |
| 2-pyrimidyl | isopropyl | methyl | methyl | bond | CH$_2$CH$_2$ | C=O(4) |
| 2-thienyl | isopropyl | methyl | methyl | bond | CH$_2$CH$_2$ | C=O(4) |
| 2-furanyl | isopropyl | methyl | methyl | bond | CH$_2$CH$_2$ | C=O(4) |
| 2-imidazolyl | isopropyl | methyl | methyl | bond | CH$_2$CH$_2$ | C=O(4) |
| 2-indolyl | isopropyl | methyl | methyl | bond | CH$_2$CH$_2$ | C=O(4) |
| 2-benzothienyl | isopropyl | methyl | methyl | bond | CH$_2$CH$_2$ | C=C(4) |
| 2-benzimidazolyl | isopropyl | methyl | methyl | bond | CH$_2$CH$_2$ | C=O(4) |
| (2-OH,4-Me)phenyl | propyl | methyl | methyl | bond | CH$_2$CH$_2$ | C=O(4) |
| (2,4-Me)phenyl | propyl | methyl | methyl | bond | CH$_2$CH$_2$ | C=O(4) |
| (2-OH)phenyl | propyl | methyl | methyl | bond | CH$_2$CH$_2$ | C=O(4) |
| (2-OH,3,4-Me)-phenyl | propyl | methyl | methyl | bond | CH$_2$CH$_2$ | C=O(4) |
| (2-OH,4-CF$_3$)-phenyl | propyl | methyl | methyl | bond | CH$_2$CH$_2$ | C=O(4) |
| (2-Cl,4-OMe)phenyl | propyl | methyl | methyl | bond | CH$_2$CH$_2$ | C=O(4) |
| (2-Cl,4-OPh)phenyl | propyl | methyl | methyl | bond | CH$_2$CH$_2$ | C=O(4) |

Remark: Numeral in ( ) means a position of $X^2$.

TABLE 18

| R¹ | R² | R⁴ | R⁵ | X¹ | Y¹ | X² |
|---|---|---|---|---|---|---|
| 1-naphthyl | propyl | methyl | methyl | bond | CH₂CH | C=O(4) |
| 2-naphthyl | propyl | methyl | methyl | bond | CH₂CH₂ | C=O(4) |
| 2-quinolyl | propyl | methyl | methyl | bond | CH₂CH₂ | C=O(4) |
| 8-quinolyl | propyl | methyl | methyl | bond | CH₂CH₂ | C=O(4) |
| 3-quinolyl | propyl | methyl | methyl | bond | CH₂CH₂ | C=O(4) |
| 2-pyrimidyl | propyl | methyl | methyl | bond | CH₂CH₂ | C=O(4) |
| 2-thienyl | propyl | methyl | methyl | bond | CH₂CH₂ | C=O(4) |
| 2-furanyl | propyl | methyl | methyl | bond | CH₂CH₂ | C=O(4) |
| 2-imidazolyl | propyl | methyl | methyl | bond | CH₂CH₂ | C=O(4) |
| 2-indolyl | propyl | methyl | methyl | bond | CH₂CH₂ | C=O(4) |
| 2-benzothienyl | propyl | methyl | methyl | bond | CH₂CH₂ | C=O(4) |
| 2-benzimidazolyl | propyl | methyl | methyl | bond | CH₂CH₂ | C=O(4) |
| (2-Cl)phenyl | isopropyl | methyl | methyl | bond | CH₂NH | C=O(4) |
| (4-Cl)phenyl | isopropyl | methyl | methyl | bond | CH₂C=O | NH(3) |
| (2-Cl)phenyl | isopropyl | methyl | methyl | bond | CH₂CH₂CH₂ | C=O(3) |
| (2,4-Cl)phenyl | isopropyl | methyl | methyl | bond | CH₂CH₂ | C=O(3) |
| (2,4-Cl)phenyl | isopropyl | methyl | ethyl | bond | CH₂CH₂ | C=O(3) |
| (3,4-Cl)phenyl | isopropyl | methyl | methyl | bond | CH₂CH₂ | C=O(3) |
| 2-benzofuranyl | propyl | methyl | methyl | bond | CH₂CH₂ | C=O(3) |
| 4-biphenylyl | propyl | methyl | methyl | bond | CH₂CH₂ | C=O(3) |

Remark: Numeral in ( ) means a position of X².

TABLE 19

| R¹ | R² | R⁴ | R⁵ | X¹ | Y¹ | X² |
|---|---|---|---|---|---|---|
| 1-OH-2-naphthyl | isopropyl | methyl | methyl | bond | CH₂CH | C=O(3) |
| (2,4-Cl)phenyl | isopropyl | methyl | methyl | bond | CH₂CH₂ | CH=CH(3) |
| 3-OH-2-naphthyl | isopropyl | methyl | methyl | bond | CH₂CH₂ | C=O(3) |
| (2-OH,4-Cl)-phenyl | isopropyl | methyl | methyl | bond | CH₂CH₂ | C=O(3) |
| (2-Cl,4-Br)-phenyl | isopropyl | methyl | methyl | bond | CH₂CH₂ | C=O(3) |
| 3-Cl-4-bi-phenylyl | isopropyl | methyl | methyl | bond | CH₂CH₂ | C=O(3) |
| (2-OH,4-Me)-phenyl | isopropyl | methyl | methyl | bond | CH₂CH₂ | C=O(3) |
| (2,4-Me)phenyl | isopropyl | methyl | methyl | bond | CH₂CH₂ | C=O(3) |
| (2-OH)phenyl | isopropyl | methyl | methyl | bond | CH₂CH₂ | C=O(3) |
| (2-OH,3,4-Me)-phenyl | isopropyl | methyl | methyl | bond | CH₂CH₂ | C=O(3) |
| (2-OH,4-CF₃)-phenyl | isopropyl | methyl | methyl | bond | CH₂CH₂ | C=O(3) |
| (2-Cl,4-OMe)-phenyl | isopropyl | methyl | methyl | bond | CH₂CH₂ | C=O(3) |
| (2-Cl,4-OPh)-phenyl | isopropyl | methyl | methyl | bond | CH₂CH₂ | C=O(3) |
| 1-naphthyl | isopropyl | methyl | methyl | bond | CH₂CH₂ | C=O(3) |
| 2-naphthyl | isopropyl | methyl | methyl | bond | CH₂CH₂ | C=O(3) |
| 2-quinolyl | isopropyl | methyl | methyl | bond | CH₂CH₂ | C=O(3) |
| 8-quinolyl | isopropyl | methyl | methyl | bond | CH₂CH₂ | C=O(3) |
| 3-quinolyl | isopropyl | methyl | methyl | bond | CH₂CH₂ | C=O(3) |
| 2-pyrimidyl | isopropyl | methyl | methyl | bond | CH₂CH₂ | C=O(3) |
| 2-thienyl | isopropyl | methyl | methyl | bond | CH₂CH₂ | C=O(3) |

Remark: Numeral in ( ) means a position of X².

TABLE 20

| R¹ | R² | R⁴ | R⁵ | X¹ | Y¹ | X² |
|---|---|---|---|---|---|---|
| 2-furanyl | isopropyl | methyl | methyl | bond | CH₂CH₂ | C=O(3) |
| 2-imidazolyl | isopropyl | methyl | methyl | bond | CH₂CH₂ | C=O(3) |
| 2-indolyl | isopropyl | methyl | methyl | bond | CH₂CH₂ | C=O(3) |
| 2-benzothienyl | isopropyl | methyl | methyl | bond | CH₂CH₂ | C=O(3) |
| 2-benzimidazolyl | isopropyl | methyl | methyl | bond | CH₂CH₂ | C=O(3) |
| (2-OH,4-Me)phenyl | propyl | methyl | methyl | bond | CH₂CH₂ | C=O(3) |
| (2,4-Me)phenyl | propyl | methyl | methyl | bond | CH₂CH₂ | C=O(3) |
| (2-OH)phenyl | propyl | methyl | methyl | bond | CH₂CH₂ | C=O(3) |
| (2-OH,3,4-Me)-phenyl | propyl | methyl | methyl | bond | CH₂CH₂ | C=O(3) |
| (2-OH,4-CF₃)-phenyl | propyl | methyl | methyl | bond | CH₂CH₂ | C=O(3) |

TABLE 20-continued

| R¹ | R² | R⁴ | R⁵ | X¹ | Y¹ | X² |
|---|---|---|---|---|---|---|
| (2-Cl,4-OMe)-phenyl | propyl | methyl | methyl | bond | $CH_2CH_2$ | C=O(3) |
| (2-Cl,4-OPh)-phenyl | propyl | methyl | methyl | bond | $CH_2CH_2$ | C=O(3) |
| 1-naphthyl | propyl | methyl | methyl | bond | $CH_2CH_2$ | C=O(3) |
| 2-naphthyl | propyl | methyl | methyl | bond | $CH_2CH_2$ | C=O(3) |
| 2-quinolyl | propyl | methyl | methyl | bond | $CH_2CH_2$ | C=O(3) |
| 8-quinolyl | propyl | methyl | methyl | bond | $CH_2CH_2$ | C=O(3) |
| 3-quinolyl | propyl | methyl | methyl | bond | $CH_2CH_2$ | C=O(3) |
| 2-pyrimidyl | propyl | methyl | methyl | bond | $CH_2CH_2$ | C=O(3) |
| 2-thienyl | propyl | methyl | methyl | bond | $CH_2CH_2$ | C=O(3) |
| 2-furanyl | propyl | methyl | methyl | bond | $CH_2CH_2$ | C=O(3) |

Remark: Numeral in ( ) means a position of $X^2$.

TABLE 21

| R¹ | R² | R⁴ | R⁵ | X¹ | Y¹ | X² |
|---|---|---|---|---|---|---|
| 2-imidazolyl | propyl | methyl | methyl | bond | $CH_2CH_2$ | C=O(3) |
| 2-indolyl | propyl | methyl | methyl | bond | $CH_2CH_2$ | C=O(3) |
| 2-benzothienyl | propyl | methyl | methyl | bond | $CH_2CH_2$ | C=O(3) |
| 2-benzimidazolyl | propyl | methyl | methyl | bond | $CH_2CH_2$ | C=O(3) |

Remark: Numeral in ( ) means a position of $X^2$.

(8) Thiazole Derivatives of the Following Formula:
The compounds of the aforementioned general formula (I) in which A is S, and Z is S.

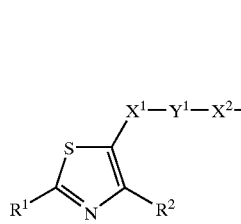

(9) Thiazole Derivatives of the Following Formula:
The compounds of the aforementioned general formula (I) in which A is S, and Z is O.

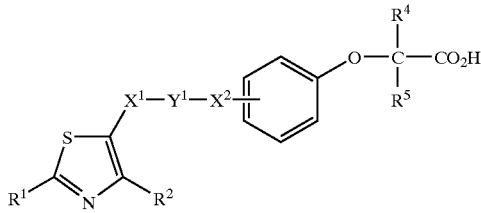

[in the formula, $R^1$, $R^2$, $R^4$, $R^5$, $X^1$, $X^2$ and $Y^1$ are those described in Tables 23 and 24].

TABLE 22

| R¹ | R² | R⁴ | R⁵ | X¹ | Y¹ | X² |
|---|---|---|---|---|---|---|
| (4-CF₃)phenyl | isopropyl | methyl | methyl | bond | $CH_2CH_2$ | C=O(4) |
| (4-Me)phenyl | propyl | methyl | methyl | bond | $CH_2CH_2$ | C=O(4) |
| (4-OMe)phenyl | butyl | methyl | methyl | bond | $CH_2CH_2$ | C=O(4) |
| (4-OPh)phenyl | hexyl | methyl | methyl | bond | $CH_2CH_2$ | C=O(4) |
| (4-OCF₃)phenyl | isopropyl | methyl | ethyl | bond | $CH_2CH_2$ | C=O(4) |
| 4-biphenylyl | propyl | methyl | methyl | bond | $CH_2CH_2$ | C=O(4) |
| (3-Me)phenyl | butyl | methyl | methyl | bond | $CH_2$ | C=O(4) |
| (3-Cl)phenyl | hexyl | methyl | methyl | bond | $CH_2CH_2$ | C=O(3) |
| (3,4-OMe)phenyl | isopropyl | methyl | methyl | bond | $CH_2CH_2$ | C=O(4) |
| (3,4-Me)phenyl | propyl | methyl | methyl | bond | $CH_2$ | CH=CH(4) |
| (3,4-Cl)phenyl | butyl | methyl | ethyl | bond | $CH_2CH_2$ | C=O(4) |
| (2,4-Me)phenyl | hexyl | methyl | methyl | bond | $CH_2CH_2$ | C=O(4) |
| (2,4-Cl)phenyl | isopropyl | methyl | methyl | bond | $CH_2CH_2$ | C=O(4) |
| (2-OH,3,4-Me)-phenyl | isopropyl | methyl | methyl | bond | $CH_2CH_2$ | C=O(4) |
| (2,4-F)phenyl | isopropyl | methyl | methyl | bond | $CH_2CH_2$ | C=O(4) |
| (2-OH,4-CF₃)-phenyl | isopropyl | methyl | ethyl | bond | $CH_2CH_2$ | C=O(3) |
| (2-F,4-OMe)-phenyl | isopropyl | methyl | propyl | bond | $CH_2CH_2$ | CH=CH(4) |
| (2-F,4-OPh)-phenyl | isopropyl | methyl | methyl | bond | $CH_2$ | C=O(4) |
| 1-naphthyl | isopropyl | methyl | propyl | bond | $CH_2$ | CH=CH (4) |

Remark: Numeral in ( ) means a position of $X^2$.

TABLE 23

| R¹ | R² | R⁴ | R⁵ | X¹ | Y¹ | X² |
|---|---|---|---|---|---|---|
| (4-CF₃)phenyl | propyl | methyl | methyl | bond | CH₂CH₂ | C=O(4) |
| (4-Me)phenyl | propyl | methyl | methyl | bond | CH₂CH₂ | C=O(4) |
| (4-OMe)phenyl | butyl | methyl | methyl | bond | CH₂CH₂ | C=O(4) |
| (4-OPh)phenyl | hexyl | methyl | methyl | bond | CH₂CH₂ | C=O(4) |
| (4-OCF₃)phenyl | isopropyl | methyl | ethyl | bond | CH₂CH₂ | C=O(4) |
| 4-biphenylyl | propyl | methyl | methyl | bond | CH₂CH₂ | C=O(4) |
| (3-Me)phenyl | butyl | methyl | methyl | bond | CH₂ | C=O(4) |
| (3-Cl)phenyl | hexyl | methyl | methyl | bond | CH₂CH₂ | C=O(3) |
| (3,4-OMe)phenyl | isopropyl | methyl | methyl | bond | CH₂CH₂ | C=O(4) |
| (3,4-Me)phenyl | propyl | methyl | methyl | bond | CH₂ | CH=CH(4) |
| (3,4-Cl)phenyl | butyl | methyl | ethyl | bond | CH₂CH₂ | C=O(4) |
| (2,4-Me)phenyl | hexyl | methyl | methyl | bond | CH₂CH₂ | C=O(4) |
| (2,4-Cl)phenyl | isopropyl | methyl | methyl | bond | CH₂CH₂ | C=O(4) |
| (2-OH,3,4-Me)-phenyl | isopropyl | methyl | methyl | bond | CH₂CH₂ | C=O(4) |
| (2,4-F)phenyl | isopropyl | methyl | methyl | bond | CH₂CH₂ | C=O(4) |
| (3,4,5-Me)-phenyl | isopropyl | methyl | ethyl | bond | CH₂CH₂ | C=O(4) |
| (2-OH,3,4-Me)-phenyl | isopropyl | methyl | propyl | bond | CH₂CH₂ | C=O(4) |

Remark: Numeral in ( ) means a position of X².

TABLE 24

| R¹ | R² | R⁴ | R⁵ | X¹ | Y¹ | X² |
|---|---|---|---|---|---|---|
| (2-OH,4-CF₃)-phenyl | isopropyl | methyl | ethyl | bond | CH₂CH₂ | C=O(3) |
| (2-Cl,4-OMe)-phenyl | isopropyl | methyl | propyl | bond | CH₂CH₂ | C=O(4) |
| (2-Cl,4-OPh)-phenyl | isopropyl | methyl | methyl | bond | CH₂CH₂ | C=O(4) |
| 1-naphthyl | isopropyl | methyl | methyl | bond | CH₂ | CH=CH(4) |
| 2-naphthyl | isopropyl | methyl | methyl | bond | CH₂CH₂ | C=O(4) |
| 2-quinolyl | isopropyl | methyl | methyl | bond | CH₂CH₂ | C=O(4) |
| 8-quinolyl | isopropyl | methyl | methyl | bond | CH₂CH₂ | C=O(4) |
| 3-quinolyl | isopropyl | methyl | methyl | bond | CH₂CH₂ | C=O(4) |
| 2-pyrimidyl | isopropyl | methyl | methyl | bond | CH₂CH₂ | C=O(4) |
| 2-thienyl | isopropyl | methyl | methyl | bond | CH₂ | CH=CH(4) |
| 2-furanyl | isopropyl | methyl | methyl | bond | CH₂CH₂ | C=O(4) |
| 2-imidazolyl | isopropyl | methyl | methyl | bond | CH₂CH₂ | C=O(4) |
| 2-indolyl | isopropyl | methyl | methyl | bond | CH₂CH₂ | C=O(4) |
| 2-benzofuranyl | isopropyl | methyl | methyl | bond | CH₂CH₂ | C=O(4) |
| 2-bonzothienyl | isopropyl | methyl | methyl | bond | CH₂CH₂ | C=O(4) |
| 2-benzimidazolyl | isopropyl | methyl | methyl | bond | CH₂CH₂ | C=O(4) |

Remark: Numeral in ( ) means a position of X².

The pharmacological effects of the invention are described below.

The PPARδ activating effect of the compound of the invention was determined by the following method:

A chimeric receptor expression plasmid (GAL4-hPPARδ LBD), a reporter plasmid (UASx4-TK-LUC) and β-galactosidase (β-GAL) are transfected into CV-1 cells by utilizing a lipofection reagent DMRIE-C (Life Technologies). Subsequently, it is incubated for 40 hours in the presence of a compound of the invention or a compound for comparison (L-165041), and then the luciferase activity and β-GAL activity are measured on the soluble cells.

The luciferase activity is calibrated by the β-GAL activity, and a relative ligand activity is calculated under the condition that the luciferase activity of the cells treated by L-165041 is set to 100%). In the same manner, relative ligand activities to PPARδ and γ transactivation activitis are calculated (see the below-mentioned Example 9).

As seen from Table 25, the compounds of the invention (Examples 1–6) show the same or higher PPARδ activating effect, as compared with L-165041. The compounds of the invention given in Examples 1 and 5 show activity to PPARδ selectively higher than activity to PPARα and γ.

Further, as seen from Table 26, the compounds of the invention (e.g., Example 7–6) show the same or higher PPARδ activating effect, as compared with L-165041. Furthermore, the compounds of the invention given in Example 7–12, etc., show activity to PPARδ selectively higher than activity to PPARα and γ.

Furthermore, as seen from Table 27, the compounds of the invention (e.g., Examples 8–1 to 8–4) show the same or higher PPARδ activating effect, as compared with L-165041.

Apparently, the compounds of the invention having the general formula (I) show excellent PPARδ activating effect. Accordingly, these compounds are expected to serve as remedy for prevention and treatment of the following diseases: hyperglycemia, hyperlipidemia, obesity, syndrome X, hyperchloresterolemia, hyperlipopreoteinemia, other dysbolismic diseases, hiperlipemia, arterial sclerosis, diseases of cardiovascular systems, hyperphagia, ischemic diseases, malignant tumors such as lung cancer, mammary cancer, colonic cancer, cancer of great intestine, and ovary cancer, Alzheimer's disease, inflammatory disease, osteoporosis (Mano H. et al., (2000) J. Biol. Chem., 175:8126–8132), Basedow's disease, and adrenal cortical dystrophy.

The compound of the invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders.

The compound of the invention can be administered to an adult generally in an amount of 0.1 mg to 100 mg a day by parenteral administration and 1 mg to 2,000 mg a day by oral administration. The dosage can be adjusted in consideration of age and conditions of the patient.

The invention is further described by the following non-limiting examples.

EXAMPLES

Example 1

2-[4-[3-[2-(2-Chlorophenyl)-5-isopropyl-4-oxazolyl]propionyl]phenyloxy]-2-methylpropionic acid (1) 4-[3-[2-(2-Chlorophenyl)-5-isopropyl-4-oxazolyl]-propionyl]phenol To an ice-cooled THF (5 mL) was added 60% sodium hydride (40 mg, 1.00 mmol). Subsequently, ethyl 2[(4-benzyloxy)benzoyl]acetate (300 mg, 1.00 mmol) was dropwise added for 30 minutes. The mixture was allowed to room temperature, and then stirred for 30 minutes. To the mixture was added 4-iodomethyl-5-isopropyl-2-(2-chlorophenyl)oxazole (362 mg, 1.00 mmol). The resulting mixture was refluxed for 20 hours and nitrogen atmosphere, and allowed to room temperature. THF was removed under reduced pressure. To the residue was added acetic acid (3.0 mL)-conc. hydrochloric acid (0.8 mL), and the mixture was refluxed for 5 hours under heating, and allowed to room temperature. The reaction mixture was poured into ice-colled water, and the aqueous mixture was extracted with ethyl acetate. The organic layer was collected, washed with a saturated aqueous sodium hydrogen carbonate solution, water, and brine, dried over anhydrous sodium sulfate, and filtered. The ethyl acetate was removed under reduced pressure, and the residue was purified by silica gel column chromatography (hexane/ethyl acetate=3/1) to give the desired compound (230 mg) as pale yellowish white crystalline product (yield 65%).

$^1$H NMR (CDCl$_3$, 400 MHz) δ: 1.32 (d, 6H, J=7 Hz), 2.96 (t, 2H, J=7 Hz), 3.15–3.50 (m, 1H), 3,27 (t, 2H, J=7 Hz), 6.78 (d, 2H, J=8 Hz), 7.1–7.2 (br, 1H), 7.3–7.4 (m, 2H), 7.45–7.50 (m, 1H), 7.79 (d, 2H, J=8 Hz), 7.90–7.95 (m, 1H).

(2) Ethyl 2-[4-[3-[2-(2-chlorophenyl)-5-isopropyl-4-oxazolyl]propionyl]phenyloxy]-2-methylpropionate In methyl ethyl ketone (5 mL) were suspended the phenol compound obtained in (1) above (220 mg, 0.59 mmol), ethyl 2-bromo-2-methylpropionate (348 mg, 1.78 mmol), and potassium carbonate (246 mg, 1.78 mmol), and the suspension was refluxed for 20 hours. The suspension was then allowed to room temperature, filtered to remove insolubles, and washed with methyl ethyl ketone. The solvent was distilled off. The residue was purified by silica gel column chromatography (hexane/ethyl acetate=4/1) to give the desired compound (230 mg) as colorless oil (yield 81%).

$^1$H NMR (CDCl$_3$, 400 MHz) δ: 1.20 (t, 3H, J=7 Hz), 1.30 (d, 6H, J=7 Hz), 1.64 (s, 6H), 2.96 (t, 2H, J=7 Hz), 3.10–3.25 (m, 1H), 3.34 (t, 2H, J=7 Hz), 4.21 (q, 2H, J=7 Hz), 6.81 (d, 2H, J=8 Hz), 7.3–7.4 (m, 2H), 7.45–7.50 (m, 1H), 7.91 (d, 2H, J=8 Hz), 7.90–7.95 (m, 1H).

(3) 2-[4-[3-[2-(2-Chlorophenyl)-5-isopropyl-4-oxazolyl]-propionyl]phenyloxy]-2-methylpropionic acid In a mixture of ethanol (6 mL) and water (3 mL) was dissolved the ester compound obtained in (2) above (220 mg, 0.45 mmol), and then lithium hydroxide monohydrate (40 mg) was added. The mixture was stirred for 20 hours at room temperature. The reaction mixture were neutralized by addition of water and diluted hydrochloric acid, and subjected to extraction using ethyl acetate. The organic layer was collected, washed with water and brine, dried over anhydrous sodium sulfate, and filtered. The ethyl acetate was removed under reduced pressure, to give 150 mg of the desired compound as colorless amorphous residue (yield 72%).

1H NMR (CDCl$_3$, 400 MHz) δ: 1.31 (d, 6H, J=7 Hz), 1.65 (s, 6H), 2.96 (t, 2H, J=7 Hz), 3.15–3.30 (m, 1H), 3.28 (t, 2H, J=7 Hz), 6.88 (d, 2H, J=8 Hz), 7.3–7.4 (m, 2H), 7.45–7.50 (m, 1H), 7.83 (d, 2H, J=8 Hz), 7.9–7.95 (m, 1H).

Example 2

2-[4-[3-[2-(4-Chlorophenyl)-5-propyl-4-oxazolyl]propionyl]phenyloxy]-2-methylpropionic acid In the same manner as in Example 1, the following intermediates and the desired compound were obtained.

(1) 4-(3-(2-(4-Chlorophenyl)-5-propyl-4-oxazolyl]-propionyl)phenol

Yield: 67%.

$^1$H NMR (CDCl$_3$, 400 MHz) δ: 0.99 (t, 3H, J=7 Hz), 1.65–1.80 (m, 2H), 2.72 (t, 2H, J=7 Hz), 2.91 (t, 2H, J=7 Hz), 3.28 (t, 2H, J=7 Hz), 6.70 (brs, 1H), 6.81 (d, 2H, J=8 Hz), 7.39 (d, 2H, J=8 Hz), 7.81 (d, 2H, J=8 Hz), 7.90 (d, 2H, J=8 Hz).

(2) Ethyl 2-[4-[3-[2-(4-chlorophenyl)-5-propyl-4-oxazolyl]propionyl]phenyloxy]-2-methylpropionate Yield: 59%.

$^1$H NMR (CDCl$_3$, 400 MHz) δ: 0.98 (t, 3H, J=7 Hz), 1.21 (t, 2H, J=7 Hz), 1.64 (s, 6H), 1.70–1.80 (m, 2H), 2.68 (t, 2H, J=7 Hz), 2.91 (t, 2H, J=7 Hz), 3.32 (t, 2H, J=7 Hz), 4.21 (q, 2H, J=7 Hz), 6.82 (d, 2H, J=9 Hz), 7.39 (d, 2H, J=8 Hz), 7.89 (d, 2H, J=8 Hz), 7.91 (d, 2H, J=9 Hz).

(3) 2-[4-[3-[2-(4-Chlorophenyl)-5-propyl-4-oxazolyl]-propionyl]phenyloxy]-2-methylpropionic acid White crystalline product Yield: 84%.

$^1$H NMR (CDCl$_3$, 400 MHz) δ: 0.98 (t, 3H, J=7 Hz), 1.68 (s, 6H), 1.70–1.80 (m, 2H), 2.70 (t, 2H, J=7 Hz), 2.91 (t, 2H, J=7 Hz), 3.24 (t, 2H, J=7 Hz), 6.89 (d, 2H, J=9 Hz), 7.39 (d, 2H, J=8 Hz), 7.89 (d, 2H, J=8 Hz), 7.89 (d, 2H, J=9 Hz).

Example 3

2-[4-[3-[2-(2-Chlorophenyl)-5-isopropyl-4-oxazolyl](1-hydroxyimino)propyl]phenyloxy]-2-methylpropionic acid (1) Ethyl 2-[4-[3-[2-(2-chlorophenyl)-5-isopropyl-4-oxazolyl](1-hydroxyimino)propyl]phenyloxy]-2-methylpropionate Ethyl 2-[4-[3-[2-(2-chlorophenyl)-5-isopropyl-4-oxazolyl]propionyl]phenyloxy]-2-methylpropionate (60 mg, 0.124 mmol) and hydroxylamine hydrochloride (26 mg, 0.372 mmol) were stirred in a mixture of pyridine (2 mL) and ethanol (3 mL) for 20 hours at room temperature. The reaction mixture was poured into water and extracted with ethyl acetate. The organic layer was collected, washed with water and brine, dried over anhydrous sodium sulfate, and filtered. The ethyl acetate was distilled off under reduced pressure to give the desired compound (45 mg) as colorless oily residue (yield 74%).

$^1$H NMR (CDCl$_3$, 400 MHz) δ: 1.20 (t, 3H, J=7 Hz), 1.22 (d, 6H, J=7 Hz), 1.58 (s, 6H), 2.86 (t, 2H, J=7 Hz), 2.95–3.05 (m, 1H), 3.31 (t, 2H, J=7 Hz), 4.19 (q, 2H, J=7 Hz), 6.78 (d, 2H, J=9 Hz), 7.30–7.40 (m, 2H), 7.40–7.50 (m, 1H), 7.53 (d, 2H, J=9 Hz), 7.95–8.00 (m, 1H).

(2) 2-[4-[3-[2-(2-Clorophenyl)-5-isopropyl-4-oxazolyl](1-hydroxyimino)propyl]phenyloxy]-2-methylpropionate The above-mentioned oxime derivative (40 mg, 0.08 mmol) was dissolved in a mixture of ethanol (2 mL) and water (1 m). To the solution was added lithium hydroxide monohydrate (10 mg). The mixture was then stirred for 20 hours at room temperature. The reaction mixture was cooled with ice and neutralized by addition of diluted hydrochloric acid. Then, ethyl acetate was added. The organic layer was collected, washed with water, dried over anhydrous sodium sulfate, and filtered. The ethyl acetate was removed under reduced pressure to give the desired compound (35 mg) as pale yellow oil (yield 92%).

$^1$H NMR (CDCl$_3$, 400 MHz) δ: 1.22 (d, 6H, J=7 Hz), 1.60 (s, 6H), 2.88 (t, 2H, J=7 Hz), 2.95–3.05 (m, 1H), 3.14 (t, 2H, J=7 Hz), 6.82 (d, 2H, J=9 Hz), 7.25–7.40 (m, 2H), 7.41 (d, 2H, J=9 Hz), 7.45–7.50 (m, 1H), 7.85–7.90 (m, 1H).

Example 4

2-[4-[3-[2-(2-Chlorophenyl)-5-isopropyl-4-oxazolyl]-1-hydroxypropyl]phenyloxy]-2-methylpropionic acid (1) 4-[3-[2-(2-Chlorophenyl)-5-isopropyl-4-oxazolyl]-1-hydroxypropyl]phenol Lithium aluminum hydride (25 mg, 0.659 mmol) was suspended in THF (5 mL). To the suspension was added 4-[3-[2-(2-chlorophenyl)-5-isopropyl-4-oxazolyl]propionyl]-phenol (240 mg, 0.65 mmol) for 3 minutes under chilling with ice. The mixture was stirred for one hour under cooling with ice, and further stirred for one hour at room temperature. To this was added saturated aqueous ammonium chloride solution under cooling with ice. The mixture was then filtered over celite. After addition of water and ethyl acetate, the organic layer was collected, washed with water, dried over anhydrous sodium sulfate, and filtered. The ethyl acetate was distilled off under reduced pressure, to give 220 mg of the desired compound as pale yellow oil residue (yield 91%).

$^1$H NMR (CDCl$_3$, 400 MHz) δ: 1.30 (d, 3H, J=7 Hz), 1.31 (d, 3H, J=7 Hz), 2.0–2.1 (m, 2H), 2.6–2.8 (m, 2H), 3.00–3.15 (m, 1H), 3.9–4.0 (br, 1H), 4.77 (t, 1H, J=6 Hz), 5.6–5.7 (br, 1H), 6.76 (2H, d, J=8 Hz), 7.23 (2H, d, J=8 Hz), 7.30–7.40 (m, 2H), 7.45–7.50 (m, 1H), 7.95–8.0 (m, 1H).

(2) 2-[4-[3-[2-(2-Chlorophenyl)-5-isopropyl-4-oxazolyl]-1-hydroxypropyl]phenyloxy]-2-methylpropionic acid The above-mentioned phenol compound (110 mg, 0.296 mmol), ethyl 2-bromo-2-methylpropionate (173 mg, 0.887 mmol), and potassium carbonate (122 mg, 0.887 mmol) were suspended in methyl ethyl ketone (3 mL). The suspension was then refluxed for 20 hours. The suspension was allowed to room temperature, filtered to remove insolubles and washed with methyl ethyl ketone. Subsequently, the solvent was distilled off. The residue was purified by silica gel column chromatography (hexane/ethyl acetate=5/1) to give ethyl 2-[4-[3-[2-(2-chlorophenyl)-5-isopropyl-4-oxazolyl]-1-hydroxypropyl]phenyloxy]-2-methylpropionate (125 mg) as colorless oil (yield 876).

The resulting propionic acid derivative (80 mg, 0.16 mmol) was dissolved in a mixture of ethanol (2 mL) and water (1 mL). To the solution was then added lithium hydroxide monohydrate (10 mg). The mixture was stirred for 20 hours at room temperature, cooled with ice, neutralized by addition of diluted hydrochloric acid, and subjected to extraction using ethyl acetate. The organic layer was collected, washed with water and brine, dried over anhydrous sodium sulfate, and filtered. The ethyl acetate was removed under reduced pressure, to give 55 mg of the desired compound as pale yellow oil residue (yield 73%).

$^1$H NMR (CDCl$_3$, 400 MHz) δ: 1.29 (d, 3H, J=7 Hz), 1.31 (d, 3H, J=7 Hz), 1.54 (s, 6H), 2.0–2.2 (m, 2H), 2.69 (t, 2H, J=7 Hz), 2.95–3.15 (m, 1H), 4.78 (t, 1H, J=7 Hz), 6.86 (d, 2H, J=8 Hz), 7.25 (d, 2H, J=8 Hz), 7.3–7.4 (m, 2H), 7.45–7.50 (m, 1H), 7.90–7.95 (m, 1H).

Example 5

2-[4-[3-[2-(2-Chlorophenyl)-5-isopropyl-4-oxazolyl]-1-propenyl]phenyloxy]-2-methylpropionic acid (1) 4-[3-[2-(2-Chlorophenyl)-5-isopropyl-4-oxazolyl]-propenyl]phenol 4-[3-[2-(2-chlorophenyl)-5-isopropyl-4-oxazolyl]-1-hydroxypropyl]phenol (110 mg, 0.296 mmol) and p-toluenesulfonic acid monohydrate (17 mg, 0.092 mmol) were refluxed in toluene (2 mL) for 20 hours. After the starting compounds diminished, the reaction mixture was poured into water and extracted with ethyl acetate. The organic layer was collected, washed with water, dried over anhydrous sodium sulfate, and filtered. The ethyl acetate was removed under reduced pressure, and the residue was purified by silica gel column chromatography (hexane/ethyl acetate=5/1), to give the desired compound (30 mg) as white crystalline product (yield 28%).

$^1$H NMR (CDCl$_3$, 400 MHz) δ: 1.34 (d, 6H, J=7 Hz), 3.10–3.20 (m, 1H), 3.45 (d, 2H, J=6 Hz), 6.15 (dt, 1H, J=6, 16 Hz), 6.34 (d, 1H, J=16 Hz), 6.36 (s, 1H), 6.70 (d, 2H, J=8 Hz), 7.09 (d, 2H, J=8 Hz), 7.3–7.4 (m, 2H), 7.4–7.5 (m, 1H), 7.95–8.00 (m, 1H).

(2) Ethyl 2-[4-[3-[2-(2-chlorophenyl)-5-isopropyl-4-oxazolyl]-1-propenyl]phenyloxy]-2-methylpropionate The above-mentioned phenol derivative 30 mg, 0.084 mmol), ethyl 2-bromo-2-methylpropionate (50 mg, 0.254 mmol), and potassium carbonate (35 mg, 0.254 mmol) were suspended in methyl ethyl ketone (3 mL), and the suspension was refluxed for 20 hours. The suspension was allowed to room temperature, filtered to remove insolubles and washed with methyl ethyl ketone. The solvent was distilled off. The residue was purified by silica gel column chromatography (hexane/ethyl acetate=5/1), to give the desired compound (28 mg) as colorless oil (yield 70%).

$^1$H NMR (CDCl$_3$, 400 MHz) δ: 1.24 (t, 3H, J=7 Hz), 1.32 (d, 6H, J=7 Hz), 1.54 (s, 6H), 3.05–3.15 (m, 1H), 3.47 (dd, 2H, J=1, 6 Hz), 4.22 (q, 2H, J=7 Hz), 6.15 (dt, 1H, J=6, 16 Hz), 6.34 (dd, 1H, J=1, 16 Hz), 6.77 (d, 2H, J=8 Hz), 7.23 (d, 2H, J=8 Hz), 7.30–7.40 (m, 2H), 7.45–7.50 (m, 1H), 7.95–8.00 (m, 1H).

(3) 2-[4-[3-[2-(2-Chlorophenyl)-5-isopropyl-4-oxazolyl]-1-propenyl]phenyloxy]-2-methylpropionic acid The above-mentioned phenol compound (110 mg, 0.296 mmol), ethyl 2-bromo-2-methylpropionate (173 mg, 0.887 mmol), and potassium carbonate (122 mg, 0.887 mmol)

were suspended in methyl ethyl ketone (3 mL). The suspension was then refluxed for 20 hours. The suspension was allowed to room temperature, filtered to remove insolubles, and washed with methyl ethyl ketone. Subsequently, the solvent was distilled off. The residue was purified by silica gel column chromatography (hexane/ethyl acetate=5/1) to give ethyl 2-[4-[3-[2-(2-chlorophenyl)-5-isopropyl-4-oxazolyl]-1-hydroxypropyl]phenyloxy]-2-methylpropionate (125 mg) as colorless oil (yield 87%).

The resulting propionic acid derivative (25 mg, 0.053 mmol) was dissolved in a mixture of ethanol (2 mL) and water (1 mL). To the solution was then added lithium hydroxide monohydrate (6 mg). The mixture was stirred for 20 hours at room temperature, and after cooling with ice, cooled with ice, neutralized by addition of diluted hydrochloric acid, and then subjected to extraction using ethyl acetate. The organic layer was collected, washed with water and brine, dried over anhydrous sodium sulfate, and filtered. The ethyl acetate was distilled off under reduced pressure, to give 15 mg of the desired compound as colorless oil residue (yield 63%).

$^1$H NMR (CDCl$_3$, 400 MHz) δ: 1.33 (d, 6H, J=7 Hz), 1.57 (s, 6H), 3.05–3.20 (m, 1H), 3.48 (dd, 2H, J=1, 6 Hz), 6.20–6.30 (m, 1H), 6.42 (dd, 1H, J=1, 16 Hz), 6.86 (d, 2H, J=8 Hz), 7.22 (d, 2H, J=8 Hz), 7.30–7.40 (m, 2H), 7.45–7.50 (m, 1H), 7.95–8.00 (m, 1H).

Example 6

2-[4-[3-[2-(2-Chlorophenyl)-5-isopropyl-4-oxazolyl]propyl]phenyloxy]-2-methylpropionic acid To a solution of ethyl 2-[4-[3-[2-(2-chlorophenyl)-5-isopropyl-4-oxazolyl]-1-propyl]phenyloxy]-2-methylpropionate (40 mg, 0.085 mmol) in ethanol (8 mL) was added 10%Pt—C (8 mg). The mixture was then stirred for 8 hours under hydrogen atmosphere (atmospheric pressure).

After the olefinic compound disappeared, water (3 mL) and lithium hydroxide monohydrate (6 mg) were added, and the mixture was stirred for 20 hours. The reaction mixture was cooled with ice and neutralized by addition of hydrochloric acid. To the neutralized mixture was added ethyl acetate. The organic layer was collected, washed with water, dried over anhydrous sodium sulfate, and filtered. The ethyl acetate was removed under reduced pressure, and the residue was purified by silica gel column chromatography (hexane/ethyl acetate=5/1), to give the desired compound (17 mg) as colorless oil (yield after two steps: 45%).

$^1$H NMR (CDCl$_3$, 400 MHz) δ: 1.29 (d, 6H, J=7 Hz), 1.56 (s, 6H), 1.85–2.05 (m, 2H), 2.56 (t, 2H, J=7 Hz), 2.65 (t, 2H, J=7 Hz), 2.95–3.10 (m, 1H), 6.87 (d, 2H, J=8 Hz), 7.11 (d, 2H, J=8 Hz), 7.30–7.40 (m, 2H), 7.45–7.50 (m, 1H), 7.90–7.95 (m, 1H).

Example 7

The following compounds were obtained by procedures similar to the procedures described in Example 1.

(7-1) 2-[4-[2-(2-Chlorophenyl)-5-isopropyl-4-oxazolyl]-methylcarbamoyl]phenyloxy-2-methylpropionic acid White crystalline product of m.p. 120–121° C.

$^1$H NMR (CDCl$_3$, 400 MHz) δ: 1.34 (6H, d, J=7 Hz), 1.65 (6H, s), 3.41 (1H, qq, J=7 Hz, 7 Hz), 4.53 (2H, d, J=6 Hz), 6.89 (2H, d, J=9 Hz), 7.2–7.4 (2H, m), 7.47 (1H, dd, J=1 Hz, 8 Hz), 7.67 (1H, dd, J=1 Hz, 8 Hz), 7.69 (2H, d, J=9 Hz), 7.79 (1H, t, J=6 Hz).

IR ν$_{max}$ (KBr) cm$^{-1}$: 3381, 3377, 2974, 1701, 1691, 1662, 1605, 1574, 1541, 1500, 1460, 1439, 1385, 1288, 1246, 1188, 1155, 1053, 1022, 966, 910, 850, 796, 766, 737, 654, 636, 592.

(7-2) 2-[4-[2-(2-Chlorophenyl)-5-isopropyl-4-oxazolyl]-acetylamino]phenyloxy-2-methylpropionic acid White amorphous product $^1$H NMR (CDCl$_3$, 400 MHz) δ: 1.35 (6H, d, J=7 Hz), 1.56 (6H, s), 3.25 (1H, m), 3.67 (2H, s), 6.88 (2H, d, J=9 Hz), 7.35–7.40 (2H, m), 7.43 (2H, d, J=9 Hz), 7.53 (1H, m), 7.93 (1H, m), 9.39 (1H, s).

(7-3) 2-[4-[4-[2-(2-Chlorophenyl)-5-isopropyl-4-oxazolyl]butyryl]phenyloxy]-2-methylpropionic acid Yellow oil $^1$H NMR (CDCl$_3$, 400 MHz) δ: 1.30 (d, 6H, J=7 Hz), 1.66 (s, 6H), 2.04 (m, 2H), 2.62 (t, 2H, J=7 Hz), 2.91 (t, 2H, J=7 Hz), 3.10 (m, 1H), 6.91 (d, 2H, J=9 Hz), 7.3–7.5 (m, 3H), 7.87 (d, 2H, J=9 Hz), 7.91 (m, 1H).

(7-4) 2-[4-[3-[2-(2,4-Dichlorophenyl)-5-isopropyl-4-oxazolyl]propionyl]phenyloxy]-2-methylpropionic acid White crystalline product of m.p. 100–105° C.

$^1$H NMR (CDCl$_3$, 400 MHz) δ: 1.30 (d, 6H, J=7 Hz), 1.65 (s, 6H), 2.95 (t, 2H, J=7 Hz), 3.20 (qq, 1H, J=7 Hz, J=7 Hz), 3.28 (t, 2H, J=7 Hz), 6.88 (d, 2H, J=8 Hz), 7.29 (dd, 1H, J=2.9 Hz), 7.49 (d, 1H, J=2 Hz), 7.85 (d, 1H, J=9 Hz), 7.85 (d, 2H, J=8 Hz).

(7-5) 2-[4-[3-[2-(2,4-Dichlorophenyl)-5-isopropyl-4-oxazolyl]propionyl]phenyloxy]-2-methylbutyric acid Microcrystalline amorphous product $^1$H NMR (CDCl$_3$, 400 MHz) δ: 1.00 (t, 3H, J=7 Hz), 1.30 (d, 6H, J=7 Hz), 1.57 (s, 3H), 1.90–2.10 (m, 2H), 2.95 (t, 2H, J=7 Hz), 3.15–3.40 (m, 3H), 6.90 (d, 2H, J=8 Hz), 7.30 (dd, 1H, J=2.9 Hz), 7.49 (d, 1H, J=2 Hz), 7.88 (d, 1H, J=9 Hz), 7.90 (d, 2H, J=8 Hz).

(7-6) 2-[4-[3-[2-(2,3-Dichlorophenyl)-5-isopropyl-4-oxazolyl]propionyl]phenyloxy]-2-methylpropionic acid White amorphous product $^1$H NMR (CDCl$_3$, 400 MHz) δ: 1.31 (d, 6H, J=7 Hz), 1.69 (s, 6H), 2.93 (t, 2H, J=7 Hz), 3.2–3.3 (m, 3H), 6.89 (d, 2H, J=9 Hz), 7.49 (d, 1H, J=8 Hz), 7.78 (dd, 1H, J=2 Hz and 8 Hz), 7.81 (d, 2H, J=9 Hz), 8.03 (d, 1H, J=2 Hz).

(7-7) 2-[4-[3-[2-(2-Benzofuranyl)-5-isopropyl-4-oxazolyl]propionyl]phenyloxy]-2-methylpropionic acid Brown microcrystalline product of m.p. 135–139° C.

$^1$H NMR (CDCl$_3$, 400 MHz) δ: 1.33 (d, 6H, J=7 Hz), 1.69 (s, 6H), 2.96 (t, 2H, J=7 Hz), 3.24 (m, 1H), 3.32 (t, 2H, J=7 Hz), 6.91 (d, 2H, J=9 Hz), 7.2–7.3 (m, 2H), 7.36 (m, 1H), 7.55 (d, 1H, J=8 Hz), 7.62 (d, 1H, J=8 Hz), 7.86 (d, 2H, J=9 Hz).

IR ν$_{max}$ (KBr) cm$^{-1}$: 2968, 1713, 1680, 1633, 1599, 1572, 1504, 1470, 1412, 1360, 1302, 1257, 1215, 1149, 1111, 1032, 964, 849, 816, 744.

(7-8) 2-[4-[3-[2-(4-Biphenylyl)-5-isopropyl-4-oxazolyl]propionyl]phenyloxy]-2-methylpropionic acid Pale yellow amorphous product $^1$H NMR (CDCl$_3$, 400 MHz) δ: 1.32 (d, 6H, J=7 Hz), 1.69 (s, 6H), 2.95 (t, 2H, J=7 Hz), 3.1–3.3 (m, 3H), 6.89 (d, 2H, J=9 Hz), 7.3–7.7 (m, 7H), 7.77 (d, 2H, J=9 Hz), 8.02 (d, 2H, J=8 Hz).

(7-9) 2-[4-[3-[2-(1-Hydroxy-2-naphthyl)-5-isopropyl-4-oxazolyl]propionyl]phenyloxy]-2-methylpropionic acid Pale yellow amorphous product $^1$H NMR (CDCl$_3$, 400 MHz) δ: 1.30 (d, 6H, J=7 Hz), 1.66 (s, 6H), 2.98 (t, 2H, J=7 Hz), 3.22 (qq, 1H, J=7 Hz, 7 Hz), 3.36 (t, 2H, J=7 Hz), 6.92 (d, 2H, J=8 Hz), 7.37 (d, 1H, J=9 Hz), 7.4–7.6 (m, 2H), 7.77 (dd, 1H, J=2, 9 Hz), 7.81 (d, 1H, J=9 Hz), 7.94 (d, 2H, J=8 Hz), 8.39 (dd, 1H, J=2, 9 Hz).

(7-10) 2-[4-[3-[2-(2,4-Dichlorophenyl)-5-isopropyl-4-oxazolyl]-1-propenyl]phenyloxy]-2-methylpropionic acid Pale Yellow oil $^1$H NMR (CDCl$_3$, 400 MHz) δ: 1.33 (d, 6H, J=7 Hz), 1.57 (s, 6H), 3.10 (m, 1H), 3.48 (dd, 2H, J=1, 6 Hz), 6.25 (m, 1H), 6.42 (dd, 1H, J=1, 16 Hz), 6.86 (d, 2H, J=8 Hz), 7.25–7.35 (m, 2H), 7.50 (d, 1H, J=2 Hz), 7.92 (d, 2H, J=8 Hz).

(7-11) 2-[4-[3-[2-(3-Hydroxy-2-naphthyl)-5-isopropyl-4-oxazolyl]propionyl]phenyloxy]-2-methylpropionic acid Yellow amorphous product $^1$H NMR (CDCl$_3$, 400 MHz) δ: 1.37 (d, 6H, J=7 Hz), 1.66 (s, 6H), 2.97 (t, 2H, J=7 Hz), 3.25 (m, 1H), 3.35 (t, 2H, J=7 Hz), 6.92 (d, 2H, J=9 Hz), 7.30 (m, 1H), 7.35 (s, 1H), 7.43 (m, 1H), 7.68 (d, 1H, J=7 Hz), 7.81 (d, 1H, J=7 Hz), 7.93 (d, 2H, J=9 Hz), 8.30 (s, 1H).

(7-12) 2-[4-[3-[2-(3-Chloro-2-hydroxyphenyl)-5-isopropyl-4-oxazolyl]propionyl]phenyloxy]-2-methylpropionic acid White amorphous product $^1$H NMR (CDCl$_3$, 400 MHz) δ: 1.31 (d, 6H, J=7 Hz), 1.67 (s, 6H), 2.94 (t, 2H, J=7 Hz), 3.20 (m, 1H), 3.31 (t, 2H, J=7 Hz), 6.90 (dd, 1H, J=2 and 9 Hz), 6.93 (d, 2H, J=9 Hz), 7.03 (d, 1H, J=2 Hz), 7.68 (d, 1H, J=9 Hz), 7.91 (d, 2H, J=9 Hz).

(7-13) 2-[4-[3-[2-(4-Bromo-2-chlorophenyl)-5-isopropyl-4-oxazolyl]propionyl]phenyloxy]-2-methylpropionic acid White amorphous product $^1$H NMR (CDCl$_3$, 400 MHz) δ: 1.30 (d, 6H, J=7 Hz), 1.65 (s, 6H), 2.94 (t, 2H, J=7 Hz), 3.20 (m, 1H), 3.26 (t, 2H, J=7 Hz), 6.87 (d, 1H, J=9 Hz), 7.43 (dd, 1H, J=2, 8 Hz), 7.65 (d, 1H, J=2 Hz), 7.76 (d, 1H, J=8 Hz), 7.83 (d, 2H, J=9 Hz).

(7-14) 2-[4-[3-[2-(3-Chloro-4-biphenylyl)-5-isopropyl-4-oxazolyl]propionyl]phenyloxy]-2-methylpropionic acid White amorphous product $^1$H NMR (CDCl$_3$, 400 MHz) δ: 1.32 (d, 6H, J=7 Hz), 1.65 (s, 6H), 2.97 (t, 2H, J=7 Hz), 3.22 (m, 1H), 3.27 (t, 2H, J=7 Hz), 6.88 (d, 2H, J=9 Hz), 7.3–7.5 (m, 3H), 7.53 (dd, 1H, J=2, 8 Hz), 7.5–7.6 (m, 2H), 7.71 (d, 1H, J=2 Hz), 7.82 (d, 1H, J=9 Hz), 7.95 (d, 2H, J=8 Hz).

Example 8

The following compound was obtained by procedures similar to the procedures described in Example 1.

(8-1) 2-[4-[3-[2-[(4-Trifluoromethyl)phenyl]-4-methyl-5-thiazolyl]propionyl]phenyloxy]-2-methylpropionic acid White crystalline product of m.p. 158–160° C.

$^1$H NMR (CDCl$_3$, 400 MHz) δ: 1.68 (s, 6H), 2.45 (s, 3H), 3.2-3.35 (m, 4H), 6.93 (d, 2H, J=9 Hz), 7.63 (d, 2H, J=9 Hz), 7.91 (d, 2H, J=9 Hz), 7.96 (d, 2H, J=9 Hz).

(8-2) The following compound was obtained by procedures similar to the procedures described in Example 1.

2-[3-[3-[2-(2,4-Dichlorophenyl)-5-isopropyl-4-oxazolyl]propionyl]phenyloxy)-2-methylpropionic acid White crystalline product of m.p. 115–120° C.

$^1$H NMR (CDCl$_3$, 400 MHz) δ: 1.31 (d, 6H, J=7 Hz), 1.62 (s, 6H), 2.92 (t, 2H, J=7 Hz), 3.16 (qq, 1H, J=7 Hz, J=7 Hz), 3.24 (t, 2H, J=7 Hz), 7.16 (dd, 1H, J=2, 9 Hz), 7.34 (dd, 1H, J=2, 9 Hz), 7.35 (t, 1H, J=9 Hz), 7.51 (d, 1H, J=2 Hz), 7.6–7.7 (m, 2H), 7.88 (d, 1H, J=9 Hz).

(8-3) 3-[2-(2,4-Dichlorophenyl)-5-isopropyl-4-oxazolyl]-1-(4-hydroxyphenyl)propan-1-one To ice-cooled THF (15 mL) was added 60% sodium hydride (120 mg, 3.00 mmol). To the mixture was dropwise added for 30 minutes a solution of ethyl 2-[(4-benzyloxy)benzoyl]acetate (900 mg, 3.02 mmol) in THF (15 mL). The resulting mixture was allowed to room temperature. The mixture was then stirred for 30 minutes, and to this was added 4-iodomethyl-5-isopropyl-2-(2,4-dichlorophenyl)oxazole (1.20 g, 3.00 mmol). The mixture was refluxed for 20 hours and nitrogen atmosphere, and then allowed to room temperature. THF was removed under reduced pressure. To the residue was added a mixture of acetic acid (7.5 mL) and conc. hydrochloric acid (2.0 mL). The resulting mixture was refluxed for 5 hours, allowed to room temperature, and poured into ice-cooled water. Ethyl acetate was added, and the organic layer was collected, washed with saturated aqueous sodium hydrogen carbonate, water and brine, dried over anhydrous sodium sulfate, and filtered. The ethyl acetate was removed under reduced pressure. The residue was purified by silica gel column chromatography (hexane/ethyl acetate=3/1), to give the desired compound (650 mg) as pale yellowish white crystalline product (yield 53%).

$^1$H NMR (CDCl$_3$, 400 MHz) δ: 1.32 (d, 6H, J=7 Hz), 2.96 (t, 2H, J=7 Hz), 3.22 (qq, 1H, J=7 Hz, 7 Hz), 3.25 (t, 2H, J=7 Hz), 6.77 (d, 2H, J=8 Hz), 7.29 (dd, 1H, J=2, 8 Hz), 7.49 (t, 1H, J=8 Hz), 7.60 (brs, 1H), 7.76 (d, 2H, J=8 Hz), 7.84 (d, 1H, J=8 Hz).

(2) 3-[2-(2,4-Dichlorophenyl)-5-isopropyl-4-oxazolyl]-1-[(4-dimethylthiocarbamoyloxy)phenyl]propan-1-one In dry dioxane (5.0 mL) were dissolved the above-mentioned phenol derivative (1.00 g, 2.47 mmol), 4-dimethylaminopyridine (30 mg, 0.25 mmol) and triethylamine (0.7 mL). To the solution was added under ice-cooling dimethylcarbamoyl chloride (367 mg, 2.97 mmol). The mixture was heated, refluxed overnight, allowed to room temperature, and poured into ice-cooled water. Ethyl acetate was added, and the organic layer was collected. The organic layer was washed with saturated aqueous sodium hydrogen carbonate solution, water and brine, dried over anhydrous sodium sulfate, and filtered. The ethyl acetate was removed under reduced pressure. The residue was purified by silica gel column chromatography (hexane/ethyl acetate=3/1), to give the desired compound (1.15 g) as pale yellow oil (yield 95%).

$^1$H NMR (CDCl$_3$, 400 MHz) δ: 1.31 (d, 6H, J=7 Hz), 2.98 (t, 2H, J=7 Hz), 3.20 (qq, 1H, J=7 Hz, 7 Hz), 3.36 (3, 3H), 3.39 (t, 2H, J=7 Hz), 3.46 (s, 3H), 7.15 (d, 2H, J=8 Hz), 7.30 (dd, 1H, J=2, 9 Hz), 7.49 (d, 1H, J=2 Hz), 7.89 (d, 1H, J=9 Hz), 8.04 (d, 2H, J=8 Hz).

(3) 3-[2-(2,4-Dichlorophenyl)-5-isopropyl-4-oxazolyl]-1-[(4-dimethylthiocarbamoylsulfanyl)phenyl]propan-1-one In n-tetradecane (15 mL) was dissolved the above-mentioned thiocarbamoyl compound (1.10 g, 2.24 mmol). The mixture was refluxed for at 250° C. (inside temperature) for 8 hours, and then allowed to room temperature. Subsequently, the reaction mixture was directly subjected to purification by silica gel column chromatography (hexane/ethyl acetate=3/1), to give the desired compound (350 mg) as pale yellow oil (yield 31%).

$^1$H NMR (CDCl$_3$, 400 MHz) δ: 1.31 (d, 6H, J=7 Hz), 2.98 (t, 2H, J=7 Hz), 3.0–3.2 (br, 6H), 3.19 (qq, 1H, J=7 Hz, 7 Hz), 3.39 (t, 2H, J=7 Hz), 3.39 (t, 2H, J=7 Hz), 7.30 (dd, 1H, J=2, 9 Hz), 7.49 (d, 1H, J=2 Hz), 7.58 (d, 2H, J=8 Hz), 7.88 (d, 1H, J=9 Hz), 7.98 (d, 2H, J=8 Hz).

(4) 3-[2-(2,4-Dichlorophenyl)-5-isopropyl-4-oxazolyl]-1-(4-mercaptophenyl)propan-1-one In dry methanol (8 mL) was dissolved the above-mentioned carbamoyl compound (335 mg, 0.68 mmol). To the solution was added 0.5N MeONa (2.0 mL). The mixture was refluxed for 20 hours and then allowed to room temperature. The reaction mixture was poured into ice-cooled water and neutralized by addition of 3N aqueous hydrochloric acid. Ethyl acetate was added, and the organic layer was collected, washed with water and brine, dried over anhydrous sodium sulfate, and filtered. The ethyl acetate was distilled off under reduced pressure, to give the desired compound (277 mg) as pale yellowish white crude solid (yield: 97%, as crude product).

$^1$H NMR (CDCl$_3$, 400 MHz) δ: 1.30 (d, 6H, J=7 Hz), 2.96 (t, 2H, J=7 Hz), 3.16 (qq, 1H, J=7 Hz, 7 Hz), 3.24 (t, 2H, J=7 Hz), 3.60 (s, 1H), 7.2–7.3 (m, 3H), 7.49 (d, 1H, J=2 Hz), 7.84 (d, 2H, J=8 Hz), 7.87 (d, 1H, J=9 Hz).

(5) 2-[4-[3-[2-(2,4-Dichlorophenyl)-5-isopropyl-4-oxazolyl]propionyl]phenylsulfanyl]-2-methylpropionic acid The desired compound was obtained using 3-[2-(2,4-dichlorophenyl)-5-isopropyl-4-oxazolyl]-1-(4-mercaptophenyl)propan-1-one obtained in (4) above by procedures similar to the procedures of (2) and (3) of Example 1.

Pale yellow amorphous product $^1$H NMR (CDCl$_3$, 400 MHz) δ: 1.30 (d, 6H, J=7 Hz), 1.52 (s, 6H), 2.97 (t, 2H, J=7 Hz), 3.19 (qq, 1H, J=7 Hz, 7 Hz), 3.37 (t, 2H, J=7 Hz), 7.29 (dd, 1H, J=2, 8 Hz), 7.48 (d, 1H, J=2 Hz), 7.55 (d, 2H, J=9 Hz), 7.86 (d, 2H, J=8 Hz), 7.90 (d, 2H, J=9 Hz).

(8-4) The following compound was obtained by procedures similar to the procedures described in Example 1.

2-[4-[3- (2-[(4-Trifluoromethyl)phenyl]-4-isopropyl-5-thiazolyl]propionyl]phenyloxy]-2-methylpropionic acid White amorphous product $^1$H NMR (CDCl$_3$, 400 MHz) δ: 1.33 (d, 6H, J=7 Hz), 1.68 (s, 6H), 3.15 (qq, 1H, J=7 Hz, 7 Hz), 3.2–3.3 (m, 4H), 6.94 (d, 2H, J=9 Hz), 7.64 (d, 1H, J=8 Hz), 7.92 (d, 2H, J=9 Hz), 7.99 (d, 2H, J=8 Hz).

Example 9

(Pharmacological Tests)

I. Method of Measurement (1) Measurement of PPARα,γ,δ Transactivation Activity

PPARα,γ,δ transactivation activity of each compound [Examples 1–6 and known PPARδ agonist (L-16504: Berger, J., et al. (1999), J. Biol. Chem., 274:6718–6725)] was measured in the manner described below.

1) Material

CV-1 was obtained from Tohoku University Aging Medical Laboratory, Medical Cell Collection Center. All test compounds were dissolved in dimethylsulfoxide (DMSO) to give a test sample of 0.1% concentration.

2) Plasmid

Receptor expression plasmid (GAL4-hPPARα, LBD GAL4-hPPARγ LBD, GAL4-hPPARδ LBD), Reporter plasmid (UASx4-TK-LUC), and β-galactosidase expression plasmid (βGAL) similar to Kliewer, S. A., et al., ((1992) Nature, 358:771–774) were employed.

3) Transfection

CV-1 cells were seeded in 24 well culture plates at 2×10$^5$ cells per well, and cultured for 24 hours using 4%-fetal bovine serum(FBS)-added OPTI-MEM I Reduced Serum Medium (Life Technologies, 500 μL/well). Subsequently, the cells were washed with non serum-added OPTI-MEM. To the washed cells were added DNA-containing solution [the following components were contained in the one well solution (250 μl): 0.03 μg of GAL4-hPPARδ LBD, 0.25 μg of UASx4-TK-LUC, 0.35 μg of βGAL, and 2 μL of lipofection reagent, DMRIE-C (Life Technologies). These components were dissolved in OPTI-MEM and allowed to stand for 30 minutes at room temperature]. The cells were incubated for 5 hours at 37° C.

4) Cell Treatment by Addition of Test Compound

The cells were then incubated for 40 hours in 500 μL of fresh OPTI-MEM containing 4% FBS and the test compound (dissolved in 100% DMSO to reach a final concentration: 10$^{-4}$M or 10$^{-5}$M).

5) Measurement of Reporter Gene Expression Level

The culture medium was removed and the cells were washed with PBS twice. Cell lysates were produced using a solubilizing buffer (25 mM Tris-PO$_4$ (pH 7.8), 15%v/v glycerol, 2% CHAPS, 1% Lecithin, 1% BSA, 4 mM EGTA (pH 8.0), 8 mM MgCl$_2$, 1 mM DTT). A portion (20 μL) of the solution was transferred onto a 96-well plate.

Subsequently, 100 μL of luciferase substrate solution (Piccagene: available from Nippon Gene Co., Ltd.) was added, and a luminous intensity per one sec. (luciferase activity) was measured by means of MLR-100 type Microluminoreader (available from Corona Electrics Co., Ltd.). Further, the activity caused by μGAL incorporation which was incorporated into the cells simultaneously with the incorporation of the luciferase gene was measured, for correcting variation of luciferase activity by the addition of the compound, utilizing the transfection efficiency of the incorporated gene. β-Galactosidase activity was measured by the following method: 50 μL of the solubilized sample was placed on another 96-well plate; 10 μL of ONPG (2-nitrophenyl-β-galactopyranoside) solution was added; incubation was carried out for 5 minutes at room temperature; 50 μL of a reaction stopping solution (1M sodium carbonate solution) was added; and the absorbance at 414 nm was measured. A relative PPAR activity was calculated based on the following: 0% (luciferase activity (control value) of cells treated with DMSO (0.1% concentration, solvent) alone), 100% (luciferase activity of cells treated with a control reagent (PPARα: 10$^{-4}$ M WY-165041, PPARγ: 10$^{-5}$ M Rosiglitazone, PPARδ: 10$^{-4}$ M L-165041)).

II. Results

The results of test are shown in Table 25.

TABLE 25

|  | PPARα | PPARγ | PPARδ |
| --- | --- | --- | --- |
| Example 1 | 9 ± 1 | 27 ± 3 | 80 ± 10 |
| Example 2 | 75 ± 4 | 51 ± 3 | 93 ± 4 |
| Example 3 | 10 | 16 | 19 |
| Example 4 | 35 | 26 | 23 |
| Example 5 | 52 ± 7 | 36 ± 3 | 114 ± 1 |
| Example 6 | 98 ± 6 | 93 ± 1 | 109 ± 10 |
| L-165041 | 2 ± 1 | 1 ± 0 | 32 ± 15 |

PPAR transactivation activity: a relative value (control = 100%)
PPARα, γ, δ transactivation activity of each compound at 10$^{-5}$ M is shown.

As is apparent from Table 25, the compounds of Examples have PPARδ transactivation activity similar to or higher than that of L-165041.

Example 10

The compounds of Example 7 were measured with respect to the PPAR activating power in the manner as described in Example 9. The results are set forth in Table 26.

TABLE 26

|  | PPARα | PPARγ | PPARδ |
| --- | --- | --- | --- |
| Example 7-4 | 1 | 2 | 86 ± 10 |
| Example 7-5 | 1 | 2 | 58 ± 14 |
| Example 7-6 | 8 | 19 | 96 ± 13 |
| Example 7-7 | 1 | 9 | 65 ± 2 |
| Example 7-8 | 1 | 26 | 58 |
| Example 7-9 | 8 | 5 ± 1 | 80 ± 5 |
| Example 7-10 | 3 | 1 | 70 |
| Example 7-11 | 29 ± 3 | 18 ± 4 | 85 ± 1 |
| Example 7-12 | 8 ± 1 | 4 | 79 ± 2 |
| Example 7-13 | 1 | 3 | 81 |
| Example 7-14 | 2 | 18 | 53 |
| L-165041 | 2 ± 1 | 1 ± 0.03 | 32 ± 15 |

As is apparent from Table 26, the compounds of the invention of Examples (Example 7–4, Example 7–6, Example 7–11, etc.) have PPARδ transactivation activity similar to or higher than that of L-165041. Further, it has been confirmed that the compounds of the invention (Example 7-4, Example 7-12, etc.) show higher PPARδ transactivation activity than PPARα-activating power and PPARγ transactivation activity power.

Example 11

The compounds of Example 8 were measured with respect to the PPAR transactivation activity in the manner as described in Example 9. The results are set forth in Table 27.

TABLE 27

|  | PPARα | PPARγ | PPARδ |
| --- | --- | --- | --- |
| Example 8-1 | 129 | 5 | 89 |
| Example 8-1 | 126 | 62 | 53 |
| Example 8-1 | 120 | 31 | 97 |
| Example 8-1 | 166 | 86 | 132 |

PPAR transactivation activity: a relative value at $10^{-5}$ M
(control = 100%)
PPARα: WY-14643 ($10^{-4}$ M)
PPARγ: Rosiglitazone ($10^{-5}$ M)
PPARδ: L-165041 ($10^{-4}$ M)

As is apparent from Table 27, the compounds of the invention (Example 8-1 to Example 8-4) have PPARδ transactivation activity similar to or higher than that of L-165041.

What is claimed is:

1. A compound having the following general formula (I) or a salt thereof:

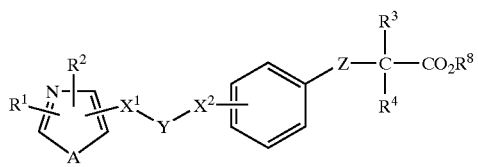

wherein $R^1$ is a hydrogen atom, an alkyl group having 1–8 carbon atoms, an alkyl group having 1–8 carbon atoms and a halogen atom substituent, an alkenyl group having 2–8 carbon atoms, an alkynyl group having 2–8 carbon atoms, a 3–7 membered cycloalkyl group, an alkyl group having 1–8 carbon atom and a 3–7 membered substituent, an arylalkyl group that has a $C_{6-10}$ aryl portion and $C_{1-4}$ alkyl portion, or an aryl or heterocyclic group which optionally has a substituent; $R^2$ is a hydrogen atom, an alkyl group having 1–8 carbon atoms, an alkyl group having 1–8 carbon atoms and a halogen atom substituent, an alkenyl group having 2–8 carbon atoms, an alkynyl group having 2–8 carbon atoms, a 3–7 membered cycloalkal group, an alkyl group having 1–8 carbon atom and a 3–7 membered substituent, an arylalkyl group that has a $C_{6-10}$ aryl portion and $C_{1-4}$ alkyl portion and optionally has a substituent, or heterocyclic group which optionally has a substituent; A is O, S, or $NR^5$ in which $R^5$ is H or $C_{1-8}$ alkyl; each of $X^1$ and $X^2$ independently is a bond, O, $S(O)_p$ in which p is an integer of 0 to 2, C(=O), C(=N—$OR^6$) in which $R^6$ is H or $C_{1-8}$ alkyl; C(=O)NH, NHC(=O), $SO_2NH$, $NHSO_2$, CH($OR^7$) in which $R^7$ is H or $C_{1-8}$ alkyl, CH=CH, or C≡C; Y is an alkylene chain having 1–8 carbon atoms and optionally a substituent; Z is O or S; each of $R^3$ and $R^4$ independently is an alkyl group having 1–8 carbon atoms and optionally a substituent; and $R^8$ is a hydrogen atom or an alkyl group having 1–8 carbon atoms; provided that $X^2$ is neither O nor $S(O)_p$ when $X^1$ is a bond, while $X^2$ is not a bond when $X^1$ is C(=O)NH.

2. An oxazole derivative having the following formula (II) or a salt thereof:

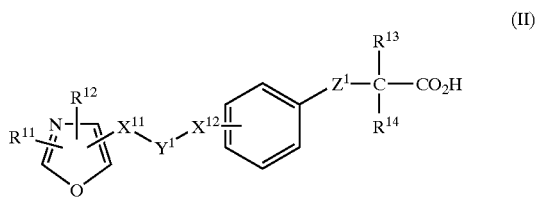

wherein $R^{11}$ is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; $R^{12}$ is an alkal group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{11}$ and $X^{12}$ independently is a bond, $S(O)_q$ in which q is an integer of 0 to 2, C(=O), C(=N—$OR^{16}$) in which $R^{16}$ is H or $C_{1-8}$ alkyl; C(=O)NH, NHC(=O), $SO_2NH$, $NHSO_2$, CH($OR^{17}$) in which $R^{17}$ is H or $C_{1-8}$ alkyl, CH=CH, or C≡C; $Y^1$ is an alkylene chain having 1–8 carbon atoms and optionally a $C_{1-8}$ alkyl or $C_{1-8}$ alkoxy substituent; $Z^1$ is O or S; each of $R^{13}$ and $R^{14}$ independently is an alkyl group having 1–8 carbon atoms and optionally a halogen or $C_{1-8}$ alkoxy substituent; provided that $X^{12}$ is neither O nor S ($O)_q$ when $X^{11}$ is a bond, while $X^{12}$ is not a bond when $X^{11}$ is C(=O)NH.

3. The oxazole derivative or the salt of claim 2, wherein $X^{11}$ is a bond.

4. The oxazole derivative or the salt of claim 2, wherein $X^{12}$ is a bond, C(=O), C(=N—OH), C(=O)NH, NHC (=O), CH(OH) or CH=CH.

5. The oxazole derivative or the salt of claim 2, wherein $R^{11}$ is a phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl.

6. The oxazole derivative or the salt of claim 2, wherein $R^{12}$ is an alkyl group having 1–8 carbon atoms, or an alkyl group having 1–8 carbon atoms and 1–3 halogen atom substituents.

7. The oxazole derivative or the salt of claim 2, wherein $R^{12}$ is attached to the 2-position of the oxazole ring.

8. A thiazole derivative having the following formula (III) or a salt thereof:

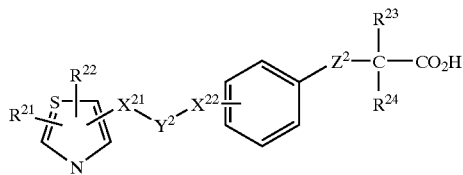

(III)

wherein each of $R^{21}$ and $R^{22}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofliranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{21}$ and $X^{22}$ independently is a bond, $S(O)_r$ in which r is an integer of 0 to 2, $C(=O)$, $C(=N-OR^{26})$ in which $R^{26}$ is H or $C_{1-8}$ alkyl; $C(=O)NH$, $NHC(=O)$, $SO_2NH$, $NHSO_2$, $CH(OR^{27})$ in which $R^{27}$ is H or $C_{1-8}$ alkyl, $CH=CH$, or $C\equiv C$; $Y^2$ is an alkylene chain having 1–8 carbon atoms and optionally a $C_{1-8}$ alkyl or $C_{1-8}$ alkoxy substituent; $Z^2$ is O or S; each of $R^{23}$ and $R^{24}$ independently is an alkyl group having 1–8 carbon atoms and optionally a halogen or $C_{1-8}$ alkoxy substituent; provided that $X^{22}$ is neither O nor $S(O)_r$ when $X^{21}$ is a bond, while $X^{22}$ is not a bond when $X^{21}$ is $C(=O)NH$.

9. The thiazole derivative or the salt of claim 8, wherein $X^{21}$ is a bond.

10. The thiazole derivative or the salt of claim 8, wherein $X^{22}$ is a bond, $C(=O)$, $C(=N-OH)$, $C(=O)NH$, $NHC(=O)$, $CH(OH)$ or $CH=CH$.

11. The thiazole derivative or the salt of claim 8, wherein $R^{21}$ is a phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$, alkoxy, $C_{1-8}$ alkoxy having 1–3 halogen substituents, phenyl, benzyl, phenyloxy, benzoyl or pyridyl.

12. The thiazole derivative or the salt of claim 8, wherein $R^{22}$ is an alkyl group having 1–8 carbon atoms, or an alkyl group having 1–8 carbon atoms and 1–3 halogen atom substituents.

13. The thiazole derivative or the salt of claim 8, wherein $R^{22}$ is attached to the 2-position of the thiazole ring.

14. A pharmaceutical composition which comprises a compound or a salt thereof defined in claim 1 and a pharmaceutically acceptable vehicle or diluent wherein said compound has the following general formula (I):

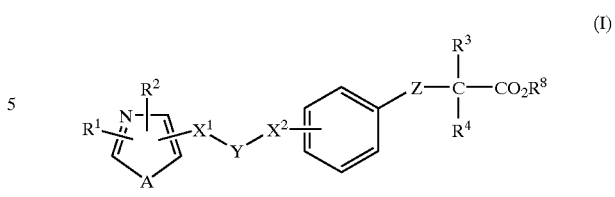

(I)

wherein $R^1$ is a hydrogen atom, an alkyl group having 1–8 carbon atoms, an alkyl group having 1–8 carbon atoms and a halogen atom substituent, an alkenyl group having 2–8 carbon atoms, an alkynyl group having 2–8 carbon atoms, a 3–7 membered cycloalkyl group, an alkyl group having 1–8 carbon atom and a 3–7 membered substituent, an arylalkyl group that has a $C_{6-10}$ aryl portion and $C_{1-4}$ alkyl portion and optionally has a substituent, or an aryl or heterocyclic group which optionally has a substituent; $R^2$ is a hydrogen atom, an alkyl group having 1–8 carbon atoms, an alkyl group having 1–8 carbon atoms and a halogen atom substituent, an alkenyl group having 2–8 carbon atoms, an alkynyl group having 2–8 carbon atoms, a 3–7 membered cycloalkyl group, an alkyl group having 1–8 carbon atom and a 3–7 membered substituent, an arylalkyl group that has a $C_{6-10}$ aryl portion and $C_{1-4}$ alkyl portion and optionally has a substituent, or a heterocyclic group which optionally has a substituent; A is O, S, or $NR^5$ in which $R^5$ is H or $C_{1-8}$, alkyl; each of $X^1$ and $X^2$ independently is a bond, O, $S(O)_p$ in which p is an integer of 0 to 2, $C(=O)$, $C(=N-OR^6)$ in which $R^6$ is H or $C_{1-8}$, alkyl; $C(=O)NH$, $NHC(=O)$, $SO_2NH$, $NHSO_2$, $CH(OR^7)$ in which $R^7$ is H or $C_{1-8}$ alkyl, $CH=CH$, or $C\equiv C$; Y is an alkylene chain having 1–8 carbon atoms and optionally a substituent; Z is O or S; each of $R^3$ and $R^4$ independently is an alkyl group having 1–8 carbon atoms and optionally a substituent; and $R^8$ is a hydrogen atom or an alkyl group having 1–8 carbon atoms; provided that $X^2$ is neither O nor $S(O)_p$ when $X^1$ is a bond, while $X^2$ is not a bond when $X^1$ is $C(=O)NH$.

15. A pharmaceutical composition which comprises a compound or a salt thereof defined in claim 2 and a pharmaceutically acceptable vehicle or diluent wherein said compound has the following formula (II):

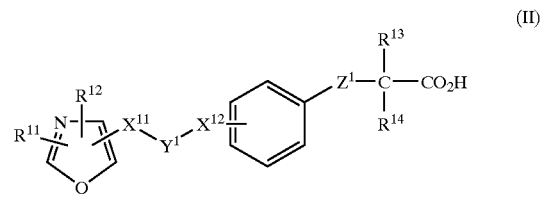

(II)

wherein $R^{11}$ is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; $R^{12}$ is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{11}$ and $X^{12}$ independently is a bond, $S(O)_q$ in which q is an integer of 0 to 2, $C(=O)$, $C(=N-OR^{16})$ in which $R^{16}$ is H or $C_{1-8}$ alkyl; $C(=O)NH$, $NHC(=O)$, $SO_2NH$, $NHSO_2$, $CH(OR^{17})$ in which $R^{17}$ is H or $C_{1-8}$ alkyl, $CH=CH$, or $C\equiv C$; $Y^1$ is an alkylene chain having 1–8 carbon atoms and optionally a $C_{1-8}$ alkyl or $C_{1-8}$ alkoxy substituent; $Z^1$ is O or S; each of $R^{13}$ and $R^{14}$ independently is an alkyl group having 1–8 carbon atoms and optionally a halogen or $C_{1-8}$ alkoxy substituent; provided that $X^{12}$ is neither O nor $S(O)_q$ when $X^{11}$ is a bond, while $X^{12}$ is not a bond when $X^{11}$ is $C(=O)NH$.

16. A pharmaceutical composition which comprises a compound or a salt thereof defined in claim 8 and a pharmaceutically acceptable vehicle or diluent wherein said compound is a thiazole derivative having the following formula (III) in a salt thereof:

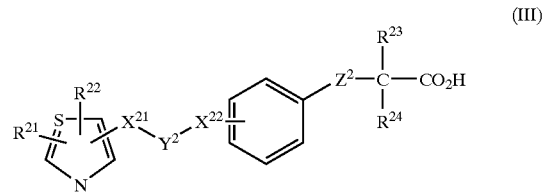

herein each of $R^{21}$ and $R^{22}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{21}$ and $X^{22}$ independently is a bond, $S(O)_r$ in which r is an integer of 0 to 2, $C(=O)$, $C(=N-OR^{26})$ in which $R^{26}$ is H or $C_{1-8}$ alkyl; $C(=O)NH$, $NHC(=O)$, $SO_2NH$, $NHSO_2$, $CH(OR^{27})$ in which $R^{27}$ is H or $C_{1-8}$ alkyl, $CH=CH$, or $C\equiv C$; $Y^2$ is an alkylene chain having 1–8 carbon atoms and optionally a $C_{1-8}$ alkyl or $C_{1-8}$ alkoxy substituent; $Z^2$ is O or S; each of $R^{23}$ and $R^{24}$ independently is an alkyl group having 1–8 carbon atoms and optionally a halogen or $C_{1-8}$ alkoxy substituent; provided that $X^{22}$ is neither O nor $S(O)_r$ when $X^{21}$ is a bond, while $X^{22}$ is not a bond when $X^{21}$ is $C(=O)NH$.

17. An oxazole derivative having the following formula (II) or a salt thereof:

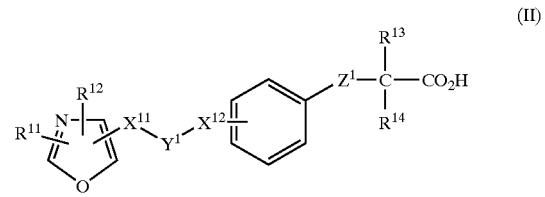

wherein each of $R^{11}$ and $R^{12}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; $X^{11}$ is attached to 4-position of the oxazole ring; each of $X^{11}$ and $X^{12}$ independently is a bond, $S(O)_q$ in which q is an integer of 0 to 2, $C(=O)$, $C(=N-OR^{16})$ in which $R^{16}$ is H or $C_{1-8}$ alkyl; $C(=O)NH$, $NHC(=O)$, $SO_2NH$, $NHSO_2$, $CH(OR^{17})$ in which $R^{17}$ is H or $C_{1-8}$ alkyl, $CH=CH$, or $C\equiv C$; $Y^1$ is an alkylene chain having 1–8 carbon atoms and optionally a $C_{1-8}$ alkyl or $C_{1-8}$ alkoxy substituent; $Z^1$ is O or S; each of $R^{13}$ and $R^{14}$ independently is an alkyl group having 1–8 carbon atoms and optionally a halogen or $C_{1-8}$ alkoxy substituent; provided that $X^{12}$ is neither O nor $S(O)_q$ when $X^{11}$ is a bond, while $X^{12}$ is not a bond when $X^{11}$ is $C(=O)NH$.

18. The oxazole derivative or the salt of claim 17, wherein $X^{11}$ is a bond.

19. The oxazole derivative or the salt of claim 17, wherein $X^{12}$ is a bond, $C(=O)$, $C(=N-OH)$, $C(=O)NH$, $NHC(=O)$, $CH(OH)$ or $CH=CH$.

20. The oxazole derivative or the salt of claim 17, wherein $R^{11}$ is a phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl.

21. The oxazole derivative or the salt of claim 17, wherein $R^{12}$ is an alkyl group having 1–8 carbon atoms, or an alkyl group having 1–8 carbon atoms and 1–3 halogen atom substituents.

22. A pharmaceutical composition which comprises a compound or a salt thereof defined in claim 2 wherein said compound is an oxazole derivative having the following formula (II) or a salt thereof:

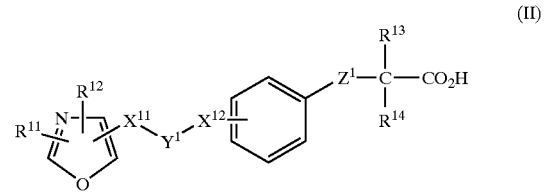

wherein each of $R^{11}$ and $R^{12}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atoms and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; $X^{11}$ is attached to 4-position of the oxazole ring; each of $X^{11}$ and $X^{12}$ independently is a bond, $S(O)_q$ in which q is an integer of 0 to 2, $C(=O)$, $C(=N-OR^{16})$ in which $R^{16}$ is H or $C_{1-8}$ alkyl; $C(=O)NH$, $NHC(=O)$, $SO_2NH$, $NHSO_2$, $CH(OR^{17})$ in which $R^{17}$ is H or $C_{1-8}$ alkyl, $CH=CH$, or $C\equiv C$; $Y^1$ is an alkylene chain having 1–8 carbon atoms and optionally a $C_{1-8}$ alkyl or $C_{1-8}$ alkoxy substituent; $Z^1$ is O or S; each of $R^{13}$ and $R^{14}$ independently is an alkyl group having 1–8 carbon atoms and optionally a halogen or $C_{1-8}$ alkoxy substituent; provided that $X^{12}$ is neither O nor $S(O)_q$ when $X^{11}$ is a bond, while $X^{12}$ is not a bond when $X^{11}$ is $C(=O)NH$.

23. A thiazole derivative having the following formula (IV) or a salt thereof:

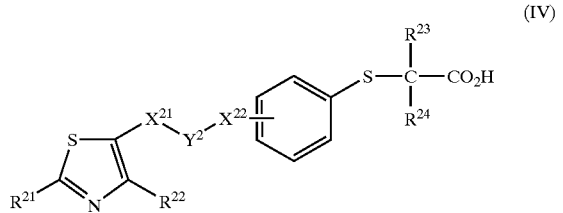

wherein each of $R^{21}$ and $R^{22}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atoms and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{21}$ and $X^{22}$ independently is a bond, $S(O)_q$ in which q is an integer of 0 to 2, $C(=O)$, $C(=N-OR^{26})$ in which $R^{26}$ is H or $C_{1-8}$ alkyl; $C(=O)NH$, $NHC(=O)$, $SO_2NH$, $NHSO_2$, $CH(OR^{27})$ in which $R^{27}$ is H or $C_{1-8}$ alkyl, $CH=CH$, or $C\equiv C$; $Y^2$ is an alkylene chain having 1–8 carbon atoms and optionally a $C_{1-8}$ alkyl or $C_{1-8}$ alkoxy substituent; each of $R^{23}$ and $R^{24}$ independently is an alkyl group having 1–8 carbon atoms and optionally a halogen or $C_{1-8}$ alkoxy substituent; provided that $X^{22}$ is neither O nor $S(O)_q$ when $X^{21}$ is a bond, while $X^{22}$ is not a bond when $X^{21}$ is $C(=O)NH$.

24. The thiazole derivative or the salt of claim 23, wherein $X^{21}$ is a bond.

25. The thiazole derivative or the salt of claim 23, wherein $X^{22}$ is a bond, $C(=O)$, $C(=N-OH)$, $C(=O)NH$, NHC($=O$), CH(OH) or $CH=CH$.

26. The thiazole derivative or the salt of claim 23, wherein $R^{21}$ is a phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl.

27. The thiazole derivative or the salt of claim 23, wherein $R^{22}$ is an alkyl group having 1–8 carbon atoms, or an alkyl group having 1–8 carbon atoms and 1–3 halogen atom substituents.

28. A pharmaceutical composition which comprises a compound or a salt thereof defined in claim 23 wherein said compound is a thiazole derivative having the following formula (IV) or a salt thereof:

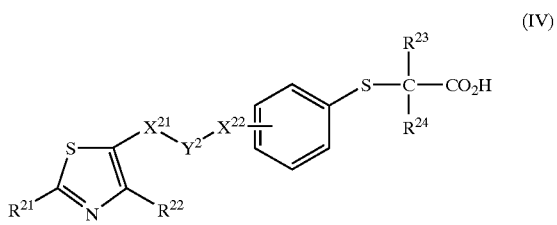

wherein each of $R^{21}$ and $R^{22}$ independently is an alkyl group having 1–8 carbon atoms, an alkyl group having 1–8 carbon atoms and 1–3 halogen atom substituents, an alkenyl group having 2–8 carbon atoms, an alkynyl group having 2–8 carbon atoms, a 3–7 membered cycloalkyl group, an alkyl group having 1–8 carbon atom and a 3–7 membered substituent, or a phenylalkyl group having $C_{1-4}$ alkyl portion, phenyl group, naphthyl group, pyridyl group, thienyl group, furyl group, quinolyl group, benzofuranyl group or benzothienyl group which optionally contains a substituent of halogen, hydroxyl, nitro, amino, $C_{1-8}$ alkyl, $C_{1-8}$ alkyl having 1–3 halogen substituents, $C_{1-8}$ alkoxy, $C_{1-8}$ alkoxy having 1–3 halogen substituents, phenyl, benzyl, phenyloxy, benzoyl or pyridyl; each of $X^{21}$ and $X^{22}$ independently is a bond, $S(O)_q$ in which q is an integer of 0 to 2, $C(=O)$, $C(=N-OR^{26})$ in which $R^{26}$ is H or $C_{1-8}$ alkyl; $C(=O)NH$, $NHC(=O)$, $SO_2NH$, $NHSO_2$, $CH(OR^{27})$ in which $R^{27}$ is H or $C_{1-8}$ alkyl, $CH=CH$, or $C\equiv C$; $Y^2$ is an alkylene chain having 1–8 carbon atoms and optionally a $C_{1-8}$ alkyl or $C_{1-8}$ alkoxy substituent; each of $R^{23}$ and $R^{24}$ independently is an alkyl group having 1–8 carbon atoms and optionally a halogen or $C_{1-8}$ alkoxy substituent; provided that $X^{22}$ is neither O nor $S(O)_q$ when $X^{21}$ is a bond, while $X^{22}$ is not a bond when $X^{21}$ is $C(=O)NH$.

29. A method of treating a disease or disorder selected from the group consisting of dysbolismic diseases, diseases of cardiovascular systems and ischemic diseases which comprises administering to a human in need thereof the compound of claim 1.

30. A method of treating a disease or disorder selected from the group consisting of dysbolismic diseases, diseases of cardiovascular systems and ischemic diseases which comprises administering to a human in need thereof the compound of claim 2.

31. A method of treating a disease or disorder selected from the group consisting of dysbolismic diseases, diseases of cardiovascular systems and ischemic diseases which comprises administering to a human in need thereof the compound of claim 8.

32. A method of treating a disease or disorder selected from the group consisting of dysbolismic diseases, diseases of cardiovascular systems and ischemic diseases which comprises administering to a human in need thereof the compound of claim 17.

33. A method of treating a disease or disorder selected from the group consisting of dysbolismic diseases, diseases of cardiovascular systems and ischemic diseases which comprises administering to a human in need thereof the compound of claim 23.

34. The method of any one of claims 26, 27, 28, 29 and 30 wherein said disease or disorder is selected from the group consisting of hyperglycemia, hyperlipidemia, obesity, syndrome X, hypercholesterolemia, hyperlipoproteinemia, hyperlipemia, arterial sclerosis, and hyperphagia.

* * * * *